United States Patent [19]

Chen et al.

[11] Patent Number: 5,753,715
[45] Date of Patent: May 19, 1998

[54] 2-DISUBSTITUTED CYCLOHEXENYL AND CYCLOHEXYL ANTIMICROBIAL AGENTS

[75] Inventors: Robert H. Chen; Maud Urbanski, both of Belle Mead; Min Xiang, Bridgewater; John Francis Barrett, High Bridge, all of N.J.

[73] Assignee: Ortho Pharmaceutical Corporation, Raritan, N.J.

[21] Appl. No.: 459,447

[22] Filed: Jun. 2, 1995

[51] Int. Cl.$^6$ .................. A61K 31/165; A61K 31/135; A61K 31/17; A61K 31/19
[52] U.S. Cl. .................. 514/655; 514/237.8; 514/274; 514/428; 514/570; 514/618; 514/619; 514/634; 514/654; 544/159; 544/162; 544/311; 548/569; 562/432; 562/473; 564/162; 564/171; 564/237; 564/367; 564/368; 564/369; 564/371; 564/374
[58] Field of Search .................. 564/238, 239, 564/162, 171, 237, 367, 368, 369, 371, 374; 514/634, 428, 237.8, 274, 570, 618, 619, 654, 655; 544/159, 162, 311; 562/432, 473; 548/569

[56] References Cited

U.S. PATENT DOCUMENTS 5,290,814   3/1994   Jackson et al. .................. 514/596

FOREIGN PATENT DOCUMENTS

WO 9115495   10/1991   European Pat. Off. .

OTHER PUBLICATIONS

Mahan, M. J., J. M. Slauch, and J. J. Mekalanos, Science, 259, 686–688 (1993).
S. Roychoudhury et al., Proc. Natl. Acad. Sci., 90, 965–969 (1993)
Inhibitors of Two–component Signal Transduction Systems: Inhibition of Alginate Gene Activation in Pseudomonas Aeruginosa.
International Search Report—International Application No. PCT/US96/10357—International Filing Date Jun. 18, 1996.
Chem. Phar. Bull. (1982), 30(10), 3601–16, XP002024094 p.3611, Line 7–Line 13 (Sohda et. al.).
J. Biol. Chem. (1992), 267(22), 15511–15, XP002024096, Huang, Jiamnin et al.
Database WPI, Section Ch, Week 9631 Derwent Publications Ltd., London, GB; Class B03, AN 96–306532 XP002024098.

*Primary Examiner*—Peter O'Sullivan
*Attorney, Agent, or Firm*—Kenneth J. Dow

[57] ABSTRACT

The invention relates to cyclohexenyl antibacterial compounds of the formula I:

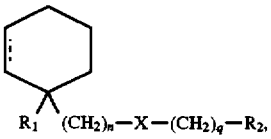

and pharmaceutical compositions containing the compounds, methods for their production and use.

17 Claims, No Drawings

2-DISUBSTITUTED CYCLOHEXENYL AND CYCLOHEXYL ANTIMICROBIAL AGENTS

BACKGROUND OF THE INVENTION

This invention relates to certain new cyclohexenyl and cyclohexyl compounds, to processes for their production, and to their use as antimicrobial agents.

It is well established that prokaryotes regulate the transcription of many of their genes in response to changes in the organisms' environment (J. B. Stock, A. M. Stock, and J. M. Mottonen, Nature, 344, 395–400 (1990)). Such regulation is essential if the organism is to adapt itself to survival in a changing environment, and pathogenic bacteria rely on such regulatory systems to enable them to survive within their host's body (J. F. Miller, J. J. Mekalanos, S. Falkow, Science, 243, 1059 (1989). Chemical compounds that interfere with the regulatory mechanisms would be expected to be useful anti-infective drugs, as they would prevent bacteria from making necessary adaptive changes in their patterns of gene expression.

Virulence, chemotaxis, toxin production, sporulation, and reproduction are examples of the bacterial processes that are under regulatory control, and which could be inhibited by such compounds. The inhibition of one or more of these processs is expected to lead to reduced virulence, a slowing or halting of bacterial growth and reproduction, and even to bacterial cell death if vital functions are interrupted.

All bacteria have two-component regulatory systems that have essentially the same type of "switch" composed of a sensor protein (a histidine protein kinase), paired with a regulatory protein (an aspartate-rich carboxylate pocket). These switches have the net effect of transmitting information from the environment to the cell nucleus, where the information is responded to by the switching on or off of transcription of relevant genes. The first step of this phosphorelay scheme relies on numerous histidine protein kinase (HPK) enzymes. Each of these HPK enzymes is a sensor molecule, and responds to stimulation by a specific environmental signal by transferring phosphate from ATP to a histidine residue of the HPK protein. This autophosphorylation is followed by transfer of the phosphate to an aspartyl residue of one or more acceptor proteins (the second components of the two-component switch), which are either regulators of gene expression (by binding to control regions on DNA, or to the RNA polymerase complex) or are themselves kinases for other acceptor molecules. These secondary acceptors may again be regulatory proteins, or kinases toward yet another protein. This cascade of phosphate from protein to protein eventually results in the phosphorylation of one or more regulatory proteins, which then control gene expression.

Thus, these proteins have been shown to control most adaptive responses of bacteria in response to stress, and are directly responsible for the ability of the bacteria to survive in the human host by expressing virulence factors encoded downstream from these regulatory "switches" (and therefore under the control of the "switches"). Inhibition of these regulatory "switches" would prevent the bacteria from growing or surviving in the host.

Recently, workers in this field reported a method for detecting bacterial "virulence" genes that are selectively expressed when bacteria infect a host (Mahan, M. J., J. M. Slauch, and J. J. Mekalanos, Science, 259, 686–688 (1993)). The potential use of this information in the design of new antibiotics was mentioned, but actual methods of reducing expression of these genes were not described. A preliminary report from another group of workers disclosed inhibitors of the two-component switch controlling alginate gene activation in Pseudomonas aeruginosa in an in vitro system (S. Roychoudhury et al., Proc. Nat. Acad. Sci., 90, 965–969 (1993)), but no anti-bacterial activity of the compounds was reported.

The compounds of the present invention are active in inhibiting histidine protein kinase, one of the components of this regulatory "switch", and are thus effective in inhibiting bacterial growth.

SUMMARY OF THE INVENTION

The invention relates to compounds of the formula I:

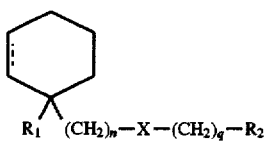

wherein:

$R_1$ is independently selected from branched or unbranched $(C_1-C_6)$alkyl, $(C_1-C_6)$ hydroxyalkyl, and a moiety of the formula:

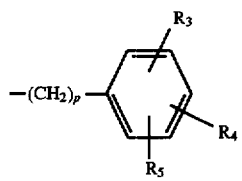

wherein:

p is an integer from 0–6; and $R_3$, $R_4$ and $R_5$ are independently selected from hydrogen, halo, $(C_1-C_4)$ alkyl, $(C_1-C_4)$ alkoxy, hydroxy, hydroxyalkyl, amino, $(C_1-C_4)$ alkylamino, and nitro;

n is an integer from 1–6;

q is an integer from 0–2;

X is selected from NH, O and S;

$R_2$ is selected from phenyl and a heterocyclic moiety wherein the heterocyclic moiety is a monocyclic heterocyclic group having 5 or 6 ring atoms and 1–4 nitrogen, oxygen, or sulfur atoms and is saturated or unsaturated, and wherein the phenyl or heterocyclic moiety is substituted with amino, moieties of the formula:

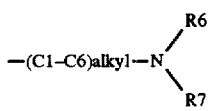

carboxy, carboxy$(C_1-C_6)$alkyl, alkyl$(C_1-C_6)$carboxy, or a moiety of the formula:

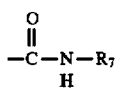

and, optionally, 1–3 substituents selected from oxo, halo, trifluoromethyl, hydroxy, -$(C_1-C_6)$ alkyl and $(C_1-C_6)$ alkoxy;

wherein $R_6$ is selected from hydrogen and $(C_1-C_6)$alkyl;

$R_7$ is selected from hydrogen, $(C_1-C_6)$ alkyl, $(C_3-C_6)$ cycloalkyl, $(C_1-C_6)$ hydroxyalkyl, $(C_1-C_6)$acyl, a moiety of the formula:

and a moiety of the formula

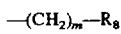

wherein m is an integer from 1–4; and $R_8$ is selected from amino, amino$(C_1-C_6)$alkyl, amino($(C_1-C_6)$alkyl$)_2$, an aryl group and a heterocyclic group wherein the aryl group is a monocyclic or bicyclic aromatic hydrocarbon group having from 6 to 10 carbon atoms and the heterocyclic group is a monocyclic or bicyclic group of 4–10 ring atoms wherein the heteroatom or heteratoms are selected from 1–4 oxygen, nitrogen or sulfur atoms and each ring of the heterocycle is composed of 4–6 atoms and is saturated or unsaturated; and the pharmaceutically acceptable alts thereof.

Preferred are compounds of the formula II:

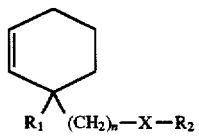

II wherein $R_1$ is selected from branched or unbranched $(C_1-C_6)$ alkyl, $(C_1-C_6)$ hydroxyalkyl, and a moiety of the formula:

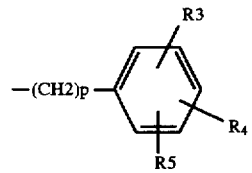

wherein:

p is an integer from 0–6;

and $R_3$, $R_4$ and $R_5$ are independently selected from hydrogen, halo, $(C_1-C_4)$ alkyl, and $(C_1-C_4)$ alkoxy;

n is an integer from 1–3;

X is NH, O or S:

$R_2$ is selected from phenyl, pyrimidine, and pyrazole and $R_2$ is substituted with amino, moieties of the formula:

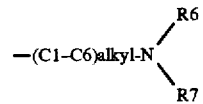

carboxy, $(C_1-C_6)$alkylcarboxy, carboxy$(C_1-C_6)$alkyl or a moiety of the formula:

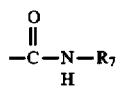

and, optionally, 1–3 substituents selected from oxo, halo, trifluoromethyl, hydroxy, -$(C_1-C_6)$ alkyl and $(C_1-C_6)$ alkoxy, wherein $R_6$ is selected from hydrogen and $(C_1-C_6)$alkyl; and $R_7$ is selected from hydrogen, $(C_1-C_6)$ alkyl, $(C_4-C_6)$ cycloalkyl, $(C_1-C_6)$ hydroxyalkyl, a moiety of the formula:

and a moiety of the formula:

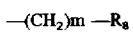

wherein m is an integer from 1–4; and $R_8$ is selected from amino, amino$(C_1-C_6)$alkyl, phenyl, benzyl, pyrrolidine, morpholine, and indole; and the pharmaceutically acceptable salts thereof.

Most preferred are compounds of the Formula II wherein:

R1 is benzyl optionally substituted with one to three substituents independently selected from halo, $(C_1-C_4)$ alkyl, and $(C_1-C_4)$alkoxy;

n is the integer 2;

X is O or $NH_2$;

$R_2$ is phenyl substituted with amino or a moiety selected from the formula:

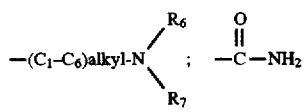

and optionally substituted with 1–2 substituents selected from halo, trifluoromethyl and hydroxy;

wherein $R_6$ is selected from hydrogen and $(C_1-C_6)$alkyl and $R_7$ is selected from hydrogen, $(C_1-C_6)$alkyl, $(C_4-C_6)$cycloalkyl, $(C_1-C_6)$ hydroxyalkyl and a moiety selected from those of the formula:

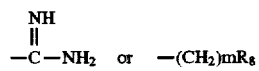

wherein m is an integer from 1–2 and $R_8$ is selected from amino, amino$(C_1-C_6)$ alkyl, phenyl, benzyl, pyrrolidine, morpholine and indole, and the pharmaceutically acceptable salts thereof.

Also included in the present invention are the dimers of the compounds of Formula I formed by the condensation of two molecules having an aminoalkyl substituent on the $R_2$ moiety as illustrated by the compounds having the structure:

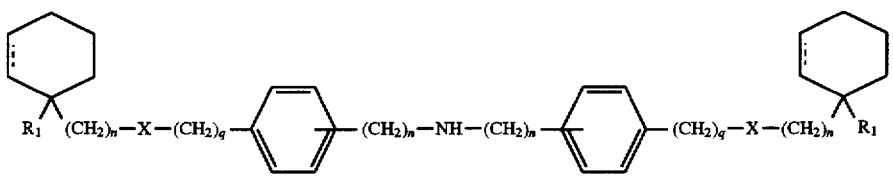

for example,3-{Bis{4-{2-{1-(3-phenylpropyl) cyclohexen-2-yl}ethoxy}phenyl1}}-1-dipropylamine.

The 2-disubstituted cyclohexenyl and cyclohexyl compounds of the present invention are inhibitors of histidine protein kinase enzyme and as such have utility as antibacterial agents in treating bacterial infections in warm-blooded animals.

DETAILED DESCRIPTION

The compounds of the present invention may generally be prepared by reacting a substituted cyclohexenyl compound of formula III with a substituted hydroxy, amino or thiol containing compound of formula IV as follows:

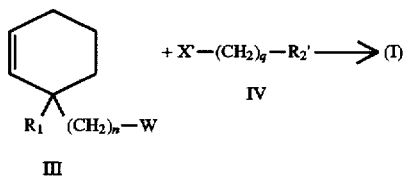

In formula III, W represents an appropriate reactive leaving group such as, for example, halo; such as chloro, bromo or iodo or a sulfonyloxy group, such as methanesulfonyloxy, trifluoromethanesulfonyloxy, benzenesulfonyloxy, 4-methylbenzenesulfonyloxy and the like leaving groups. In formula IV, X' is hydroxy, a primary or secondary amine, or a thiol group, depending on the nature of the moiety X in the final compound.

$R_2'$ may be any of the moieties of $R_2$ or, as shown in the following Scheme 2, particularly in the case where $R_2$ is a substituted phenyl or substituted heterocyclic moiety. $R_2$ may be an intermediate such as a (hydroxyalkyl) phenyl moiety, 9', which may be further reacted with, for example, a secondary amine, to yield the final compounds having further substituents, like an (alkylamino) compound 11, on the phenyl or heterocyclic moiety of $R_2$.

The reaction can be conveniently carried out by mixing the reactants in an inert solvent such as hexane, diethyl ether, toluene, tetrahydrofuran and the like under appropriate, temperatures from room temperature or below up to the boiling point of the solvent used. The products are isolated by filtration or by evaporation of the solvent and they may be purified by recrystallization, absorption chromatography or distillation under reduced pressure. The substituted cyclohexenyl starting material of Formula II may be prepared in accordance with Scheme I in which the 3-ethoxy-2-cyclohexanone compound of formula 1 is reacted with the Grignard reagent or an alkyllithium compound derived from the alkyl, protected hydroxyalkyl or phenyl moiety $R_1$, to yield the substituted 2-cyclohexanone compound 2. The reaction may conveniently be conducted in an appopriate solvent, such as, for example ether or tetrahydrofuran. Elevated temperatures may be appropriate to enhance the reaction rate. This compound is then reduced with a reducing agent such a sodium borohydride, lithium aluminum hydride or the like in suitable solvents such as alcohols, THF or ether to yield the hydroxy cyclohexenyl compound 3. The hydroxy cyclohexenyl intermediate 3 is then converted to the alkylhydroxy cyclohexenyl compound 6 by reacting 3 with either (a) sodium hydride/phenylvinylsulfoxide or (b) triethyl orthoester followed by reduction of the resulting intermediate 3a with a reducing agent such as sodium borohydride or lithium aluminum hydride or the like, to yield the hydroxyalkylcyclohexenyl intermediate 6.

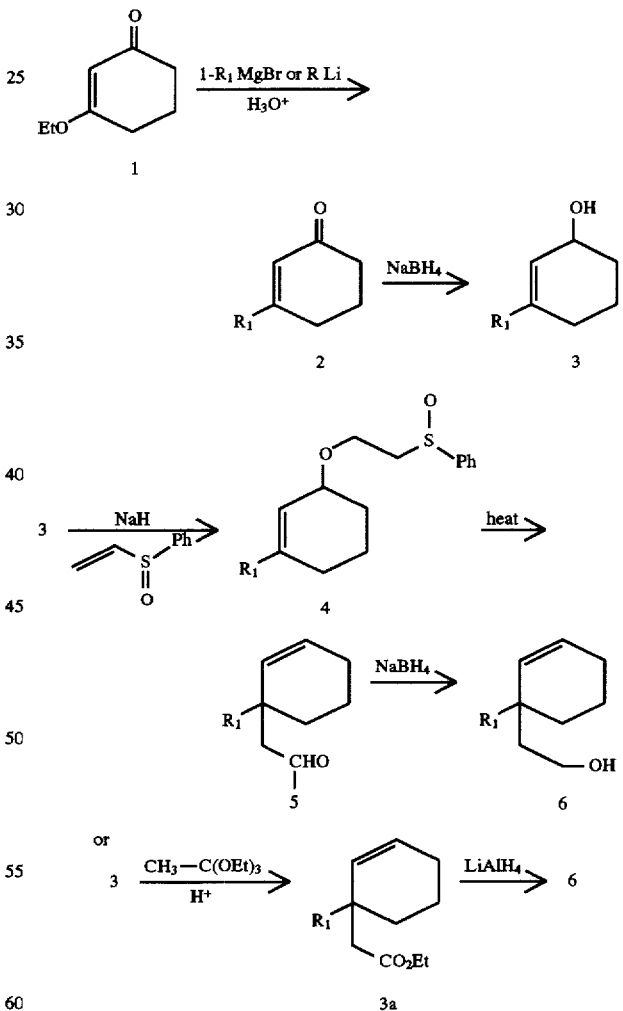

Preparation of the compounds of the present invention is further illustrated in Schemes 2-6. As can be seen from the reaction Scheme 2, the ether linked compounds where X is oxygen are conveniently prepared by reacting the substituted hydroxyalkyl cyclohexenyl intermediate 6 with a reagent capable of converting the alcohol function into a reactive leaving group W, for example halo or methanesulfonyl chloride and the like. The resulting compound 7 is then reacted with the appropriate phenol 8; such as 4-hydroxy phenethyl alcohol to yield the cyclohexenyloxy compound 9. The reaction is generally carried out in the presence of a base, such as, potassium carbonate, potassium hydroxide, sodium hydroxide, and the like at temperatures of room temperature to reflux.

To further illustrate, the methanesulfonyl compound 7 may be reacted with the (hydroxyalkyl) phenol compound 8' to yield the cyclohexenyl phenoxy compound 9'. This compound may be further reacted with methanesulfonyl chloride in the presence of triethylamine to form the methanesulfonate intermediate 10, which can be reacted with ammonia or a primary or secondary amine to obtain the amino compound 11. Alternatively, the amino compound 11 can be obtained directly by reacting the cyclohexenyl methanesulfonyl intermediate 7 with an alkylaminophenol compound 14 or 15 under basic conditions, such as in the presence of potassium carbonate, potassium hydroxide or sodium hydroxide. The guanidino compound 13 may be prepared by reacting the amino derivative 12 with 3,5-dimethylpyrazole-1-carboxamidine nitrate in N,N-dimethyl formamide at room temperature to 100° C.

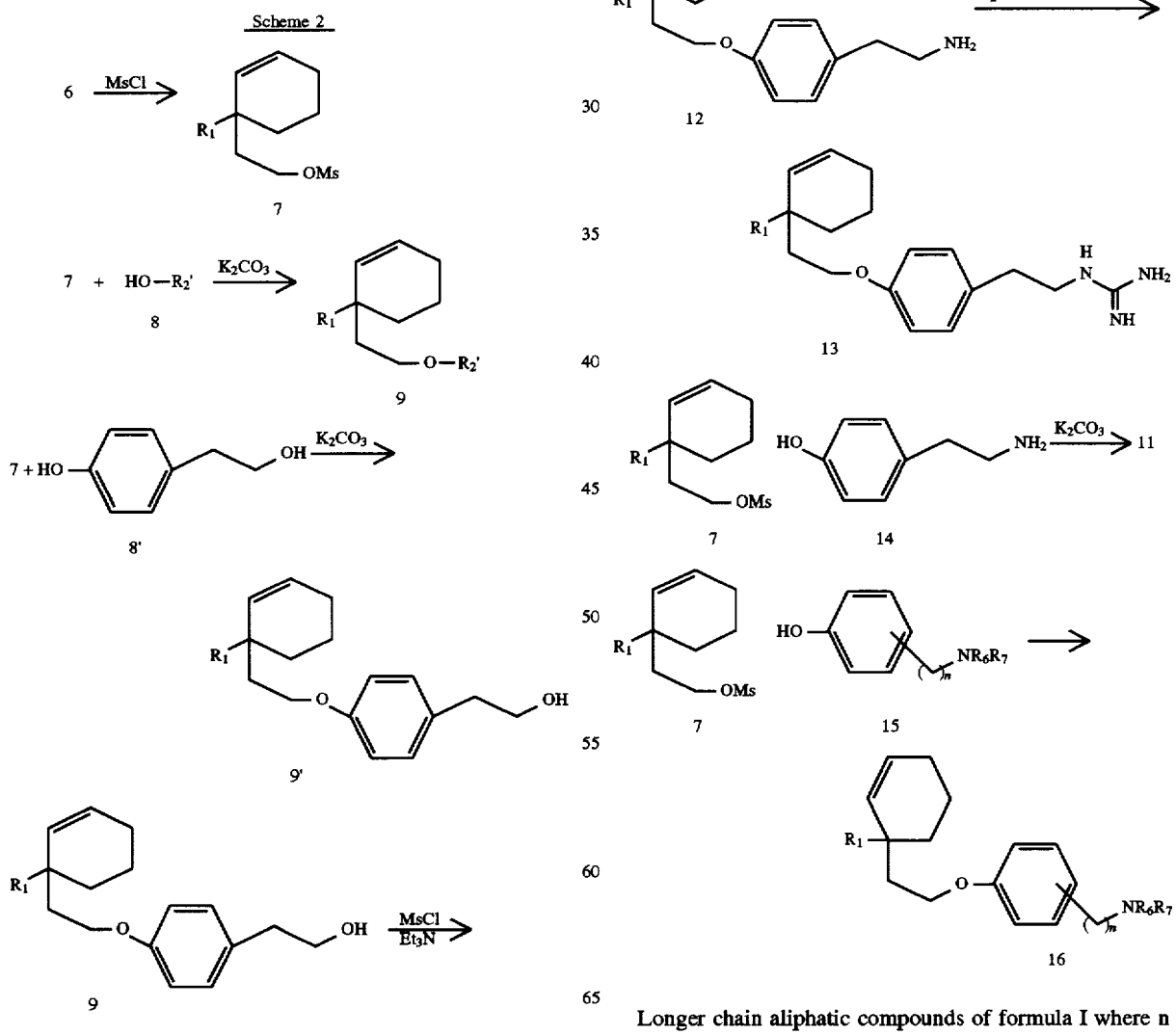

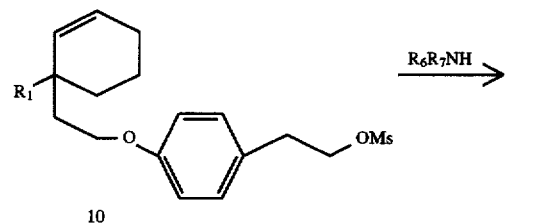

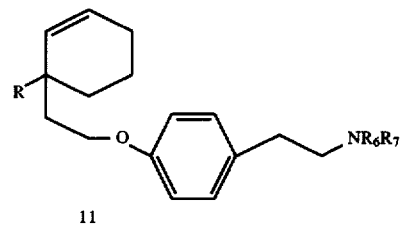

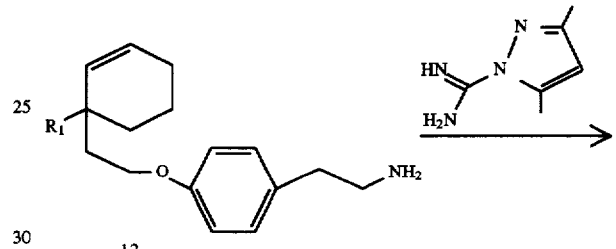

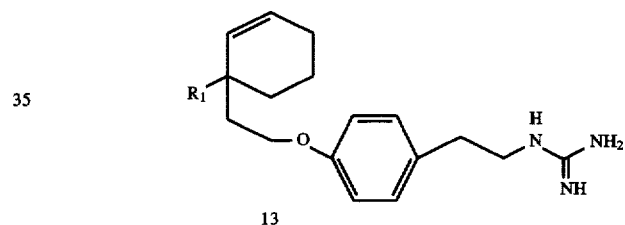

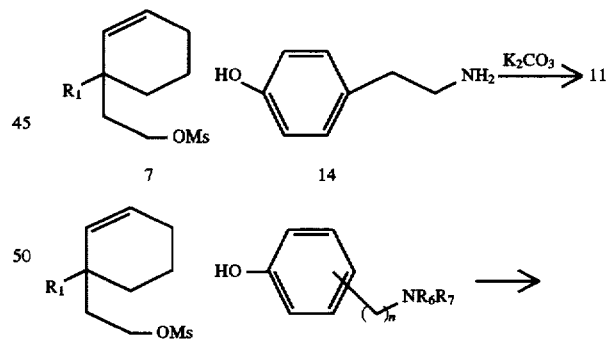

Longer chain aliphatic compounds of formula I where n is 3 or 4 are prepared in accordance with Scheme 3 wherein the cyclohexenyl methanesulfonate intermediate 7 is reacted with potassium cyanide to yield the cyano intermediate 17. The cyano intermediate 17 is converted to intermediate 18 in three steps by hydrolysis of 17 with a base such as aqueous sodium hydroxide, aqueous potassium hydroxide, or the like, followed by reaction with a reducing agent such lithium aluminum hydride or diborane in tetrahydrofuran and finally reacting the alcohol intermediate with methanesulfonyl chloride in triethylamine.

The compounds wherein n=4 are obtained by reacting 7 with sodium hydride and diethyl malonate to yield the diester 19. The intermediate 19 is converted to the methanesulfonyl compound 20 by hydrolysis with an aqueous base such as sodium hydroxide at temperatures of room temperature to 80° C. followed by decarboxylation at about 180° C. The mono acid is reduced with lithium aluminum hydride or the like and then reacted with methanesulfonyl chloride in triethyl amine. 18 or 20 are converted to the final compounds by the procedures of Scheme 2.

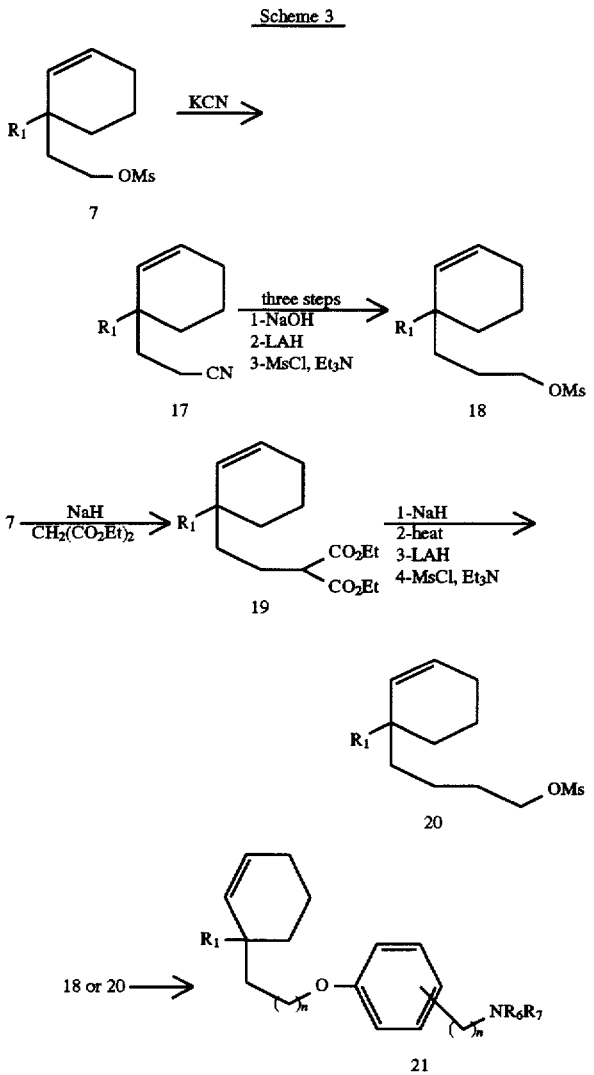

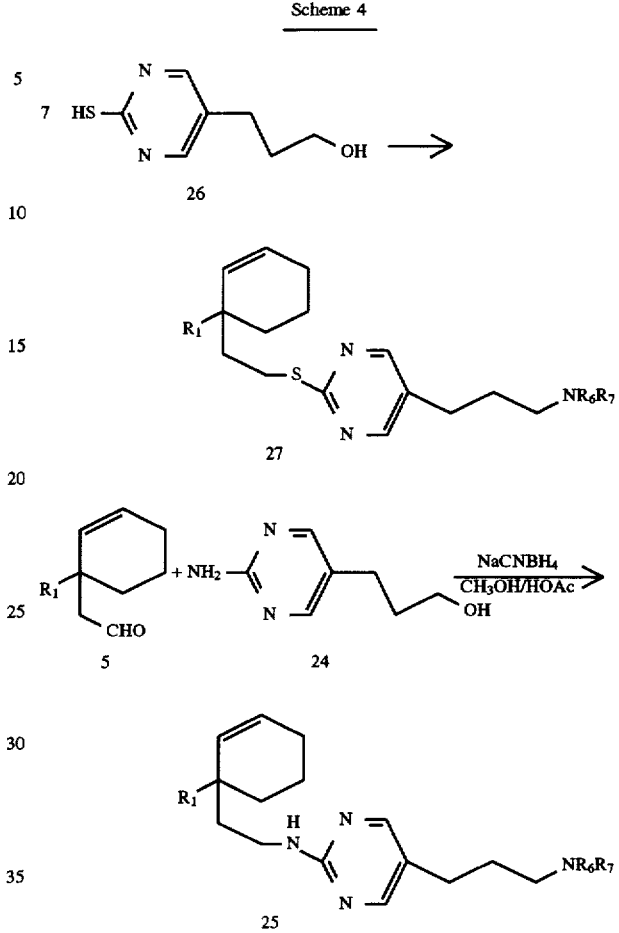

Those compounds wherein X is sulfur, can be prepared in accordance with Scheme 4 by reacting the cyclohexenyl methanesulfonyl intermediate 7 with the appropriate thiol reagent. So, for example, the thiol compound 27 can be prepared from reaction of the thiol derivative 26 with the cyclohexenyl intermediate 7.

In contrast, those compounds where X is a relatively weak acidic nitrogen function such as aniline or aminopyridine may be obtained from the aldehyde 5 by the reductive amination procedure. Accordingly, as shown in Scheme 4, compound 25 may be obtained from aldehyde 5 by reacting the aminopyridine compound 24 with 5 in the presence of sodium cyanoborohydride in methanol/acetic acid to obtain the amino derivative 25.

The saturated cyclohexyl compounds of Formula I may be prepared in accordance with Scheme 5 by hydrogenation of the cyclohexenyl compound using conventional catalytic hydrogenation techniques, such as, for example, with hydrogen under pressure using 10% palladium on carbon in a suitable solvent such as triflouroacetic acid.

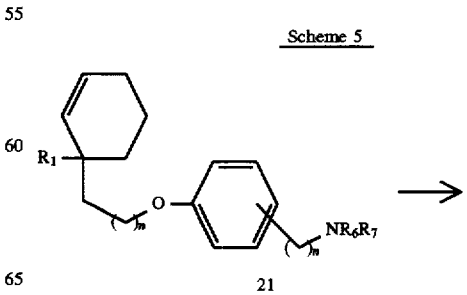

-continued
Scheme 5

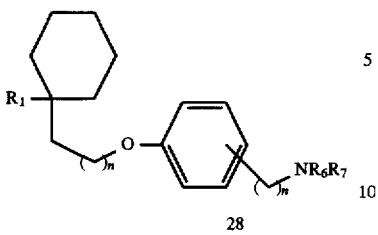

28

The reactions are performed in a solvent appropriate to the reagents and materials employed and suitable for the transformation being effected. It is understood by those skilled in the art of organic synthesis that the various functionalities present on the molecule must be consistent with the chemical transformations proposed. This will frequently necessitate judgment as to the order of synthetic steps, reactive groups, and reaction conditions. Reaction conditions compatible with the substituents employed will be apparent to one skilled in the art.

From formula (I) it is evident that some of the compounds of the invention may have one or more asymmetrical carbon atoms in their structure. It is intended that the present invention include within its scope the stereochemically isomeric forms of the compounds as well as their racemates. Pure sterochemically isomeric forms may be obtained by the application of art known principles. Diastereoisomers may be separated by physical separation methods such as fractional crystallization and chromatographic techniques and enantiomers may be separated from each other by the selective crystallization of the diasteromeric salts with optically active acids. Pure stereoisomers may also be prepared synthetically from the corresponding pure isomers by using stereospecific reactions.

Suitable pharmaceutical salts are those of inorganic or organic acids, such as, hydrochloric acid, hydrobromic acid, hydroiodic acid, sulfuric acid, nitric acid, phosphoric acid, acetic acid, succinic acid, oxalic acid, malic acid and the like. Suitable salts are furthermore those of inorganic or organic bases, such as KOH, NaOH, Ca(OH)$_2$, Al(OH)$_3$, piperidine, morpholine, ethylamine, triethylamine and the like.

Also included within the scope of the invention are the hydrated forms of the compounds which contain various amounts of water, for instance, the hydrate, hemihydrate and sesquihydrate forms.

The compounds of the present invention have antibacterial activity as determined by the following tests. First, the compounds are tested for their activity in inhibiting the autophosphorylation of Kinase A and the transphosphorylation of SPoOF, two proteins involved in the signal transduction system controlling regulatory gene expression in bacteria. Representative compounds are then tested for antibacterial activity against selected pathogenic organisms by the MIC method. The results are set forth below.

I. Autophosphorylation of Kinase A and Transphosphorylation of SPoOF Assay

To study the effect of the compounds of the present invention on the signal transduction process in bacteria, the inhibiting effect of the compounds on the sporulation operon proteins Kinase A and SpoOF was examined. Specifically, the inhibition of autophosporylation of Kinase A and the transphosphorylation of SpoOF was determined in the following assays. The SpoOF response regulator is the primary substrate for phosporylation by the protein kinase, Kin A, involved in the sporulation process in bacteria. See D. Burbulys, K. A. Trach, J. A. Hoch, Cell, 64, 545–552 (1991).

The following stock reagents were either prepared and used promptly or stored at the indicated temperature:

8×Salts: 2M KCl (5 mL), 1M MgCl$_2$ (800 mL), 1M CaCl$_2$ (100 mL), 10 mg/mL phenylmethylsulfonyl fluoride (200 mL), 1M dithioreitol (50 mL), 0.25M Na$_2$EDTA (32 mL) and H$_2$O 3.82 mL (−20° C.)

5×Loading Dye: 0.5M TRIS-HCl-pH 6.8 (7.5 mL), 10% SDS (2 mL) 0.1% bromophenol blue (0.5 mL), 100% glycerol (3 mL) and 12.5M b-mercaptoethanol (0.3 mL)

1–1.3 mg/mL KinA: 15 mM TRIS-HCl, pH 8.0, 6 mM KCl; 4 mM b-mercaptoethanol; 40% glycerol (−20° C.)

1 mg/mL SpoOF: 17.5 mM TRIS-HCl, pH 8.0; 0.7 mM KCl; 0.7 mM MgCl$_2$; 0.7 mM CaCl$_2$; 5mM b-mercaptoethanol; 30% Glycerol (−20° C.)

5% Stacking Gel: 40% 29:1 acrylamide:bis acrylamide (1.25 mL), 0.5M TRIS-HCl, pH 6.8 (2.5 mL), 10% SDS (0.1 mL), D-H$_2$O (6.15 mL) 10% ammonium persulfate (100 mL) and TEMED (25 mL)

SDS Running Buffer. TRIS-BASE (3.02 g, Sigma), glycine (14.4 g, Sigma) SDS (1 g, SERVA), D-H$_2$O (to 1 L)

The reaction mixture was prepared from 8×Salts (87 mL), 1M TRIS, pH 8 (87 mL), 50% glycerol (63 mL), 2% gelatin (31 mL), SPoOF (14.1 mL) and KinA (7.0 mL). Microcentrifuge tubes were filled with the reaction mixture (18.5 mL) as well as 1 mM solution of the test compound in DMSO (18.5 mL) and incubated for 15 min on ice. Add 100 mM [$^{32}$P]ATP/ATP solution (625 mCi, 3.0 mL) and leave for 10 minutes at room temperature. Quench the reaction with 5×loading dye (10 mL/per tube) and either load the samples on a prepared 5% Stacking Gel or store on dry ice until ready for use. Fill the prepared wells with SDS Running Buffer, load samples in the wells, add the upper buffer chamber and place in a tank filled with SDS Running Buffer. Apply 80 volts (Hoeffer Unit) until the dye front reaches the bottom of the stacking gel and then increase the voltage to 250 volts until electrophoresis is complete.

If either enzyme is inhibited (determined by their absence in the developed gel), an IC 50 is calculated by running predetermined inhibitor concentrations (500, 250, 125, 62.5, 31.3, 15.7 and 7.9 mM). The % inhibition is determined by measuring the concentration of radioactive phosphorus with a phosphoimager and calculating the values using a oftware program (Biorad Molecular Analyst).

| Results |||
|---|---|---|
| Compound # | IC min (mM) | IC$_{50}$ (mM) |
| 1 | 62.5 | 210 |
| 3 | 31.25 | 159 |
| 5 | 15.6 | 18.5 |
| 6 |  | 35.8 |
| 7 |  | 330 |
| 8 |  | 92.3 |
| 9 | 250 | 446 |
| 10 | 125 | 257 |
| 11 | 125 | 353 |
| 12 | 125 | 354 |
| 13 | 7.8 | 39.5 |
| 14 | 500 |  |
| 15 | 125 | 432 |
| 16 | 15.6 | 43.5 |

-continued

| Compound # | IC min (mM) | IC$_{50}$ (mM) |
|---|---|---|
| 17 | 15.6 | 38.3 |
| 18 | 125 | 261 |
| 19 | 62.5 | 82.1 |
| 20 |  | 122 |
| 21 | 500 | 728 |
| 22 | 31.25 | 94.7 |
| 23 | 125 | 295 |
| 24 | 125 | 185 |
| 25 | 125 | 200 |
| 26 | 250 | 437 |
| 27 | 125 | 318 |
| 28 | >1000 | 9999 |
| 29 | 250 | 385 |
| 30 | 125 | 145 |
| 31 | 62.5 | 91 |
| 32 | 125 | 164 |
| 33 | 125 | 339.5 |
| 34 | 125 | 295 |
| 35 | 125 | 468.4 |
| 36 | 500 |  |
| 37 | 62.5 | 107.7 |
| 38 | 125 | 164.1 |
| 39 | 31.25 | 61.5 |
| 40 | 31.25 | 46.8 |
| 41 | 31.25 | 82.5 |
| 42 | 62.5 | 139 |
| 43 | 125 | 210 |
| 44 | 62.5 | 133 |
| 45 | 15.6 | 17.9 |
| 46 | 15.5 | 28.2 |
| 47 | 15.6 | 21 |
| 48 | 500 |  |
| 49 |  | 162 |
| 50 |  | 112.8 |
| 51 | >1000 | 9999 |
| 52 |  | 174 |
| 53 |  | 113 |
| 54 |  | 122 |
| 55 |  | 91.3 |
| 56 |  | 66.6 |
| 57 |  | 46.6 |
| 58 |  | 74.8 |
| 59 |  | 46.1 |
| 60 | 62.5 | 98 |
| 61 | 62.5 | 94.6 |

II. MIC Antimicrobial Activity

Procedure

The in vitro antimicrobial spectrum of the compounds of the present invention were determined by the microdilution broth method following the test method from the National Committee for Laboratory Standards (NCCLS). The method is described in the NCCLS Document M7-A2, Vol. 10, No.8 "Methods for Dilution Antimicrobial Susceptibility Test for Bacteria that Grow Aerobically—Second Edition".

In this method two fold serial dilutions of drug in cation supplemented Mueller Hinton broth are added to wells in microdilution trays. The test organisms are prepared by adjusting the turbidity of actively growing broth cultures so that the final concentration of test organism after it is added to the wells is approximately 5×10$^4$ colony forming units per well delivered by the Steers replicating device.

Following inoculation of the microdilution trays, the trays are incubated at 35° C. for 16–20 hours and then read. The minimal inhibitory concentration (MIC) is the lowest concentration of antimicrobial that completely inhibits growth of the test organism. The amount of growth in the wells containing the test compound is compared with the amount of growth in the growth-control wells used in each tray.

| Cpd. # | E. coli oc2605 | E. coli oc2530 | K. pneum. oc1943 | Ps. aerug. oc161 | Ps. aerug. oc27853 |
|---|---|---|---|---|---|
| 17 | 64 | 8 | >64 | >64 | >64 |
| 3 | 16 | 8 | 32 | >64 | >64 |
| 24 | >64 | 8 | >128 | >128 | >128 |
| 34 | 8 | 4 | 32 | >64 | >64 |
| 41 | >64 | 4 | >128 | >128 | >128 |
| 49 | 128 | 16 | 128 | 128 | 128 |
| 53 | >64 | 16 | >128 | >128 | >128 |
| 59 | ≥64 | 16 | >128 | >128 | >128 |
| OFX | ≤0.12 | ≤0.12 | 0.25 | 2 | 8 |
| MN | >128 | >32 | 32 | >128 | >128 |

| Cpd. # | C. albicans 10231 | C. tropicalis | A. niger 10578 | E. faecalis ACTCC 29212 | E. faecalis oc3041 |
|---|---|---|---|---|---|
| 17 | ≤16 | 4 | 4 | 8 | 8 |
| 3 | >64 | 8 | 4 | 8 | 8 |
| 24 | 8 | 8 | 4 | 8 | 8 |
| 34 | 8 | ≤4 | 8 | 4 | 4 |
| 41 | 8 | 4 | 2 | 8 | 8 |
| 49 | 32 | 16 | 16 | 32 | 32 |
| 53 | 4 | 2 | 8 | 4 | 8 |
| 59 | 8 | 8 | 44 | 8 | 8 |
| OFX | >128 | >128 | >128 | 2 | 2 |
| MN | 2–≥32 | 8 | 2 | 8 | 8 |

| Cpd. # | E. faecium oc2993 | MRSA oc2089 | MRSA oc667 | S. aureus ATCC 29213 | S. epi oc2603 |
|---|---|---|---|---|---|
| 17 | 8 | 8 | 8 | 8 | 8 |
| 3 | 8 | 8 | 8 | 8 | 8 |
| 24 | 8 | 8 | 8 | 8 | 8 |
| 34 | 4 | 4 | 4 | 4 | 4 |
| 41 | 8 | 8 | 8 | 8 | 8 |
| 49 | 32 | 32 | 32 | 64 | 16 |
| 53 | 8 | 4 | 8 | 4 | 8 |
| 59 | 8 | 8 | 8 | 8 | 8 |
| OFX | 4 | 4 | 0.5 | 0.5 | 2 |
| MN | 8 | 8 | 8 | 8 | 2 |

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacological acceptable salt can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, preferably given in divided doses two to four times a day, or in sustained release form. For most large mammals the total daily dosage is from about 0.07 g to 7.0 g, preferably from about 100 mg to 1000 mg Dosage forms suitable for internal use comprise from about 100 mg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

This invention further provides a method of treating bacterial infections in warm-blooded animals, which comprises administering to the animals a compound of the invention alone or in admixture with a diluent or in the form of a medicament according to the invention.

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

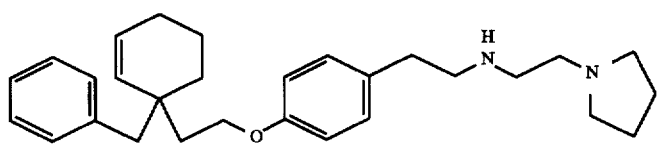

Compound 1

2-[3-[4-[2-[1-BENZYL(2-CYCLOHEXENYL)]]ETHOXY]PHENYL-
ETHYL]AMINOETHYLPYRROLIDINE MONOOXALATE HEMIHYDRATE.

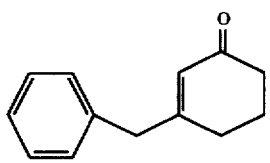

1A

3-Ethoxy-2-cyclohexen-1-one (182 g, 1.3 mol) was added dropwise to a stirred solution of 2.0M benzylmagnesium chloride (800 mL, 1.6 mol) in ether (200 mL) at 0° C. under $N_2$. The resulting mixture was stirred for a total of 5 h at 0° C., quenched with 30% $H_2SO_4$ aq. (350 mL) and stirred at room temperature for 16 h. The mixture was extracted with several portions of $CH_2Cl_2$ and the combined organic extracts were concentrated in vacuo to give compound 1A as an oil (130.0 g).

1B

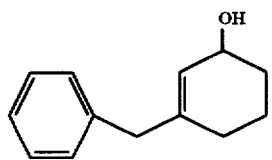

Compound 1A (130 g, 0.7 mol) was added dropwise, via an addition funnel, to a stirred mixture of LAH (13.28 g, 0.7 mol) and ether (400 mL) under $N_2$ at 0° C. When addition was complete, the addition funnel was rinsed with ether (200 mL) to remove an residual reactant and the reaction was stirred for another 5 h. The reaction mixture was quenched by the addition of saturated aqueous $K_2CO_3$ and left to stir at room temperature for 16 h. The resulting mixture was filtered through celite, dried ($Na_2SO_4$) and concentrated in vacuo to give the alcohol 1B as an oil (134.2 g.).

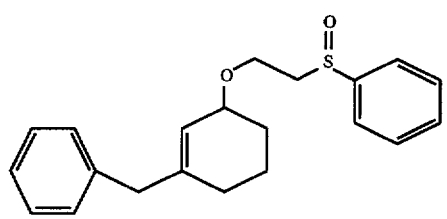
1C

Sodium hydride (4.5 g, 0.19 mol) was added portionwise to a solution of alcohol 1B (70.1 g, 0.373 mol) in THF (600 mL) at room temperature under $N_2$. The mixture was stirred for 30 min, phenyl vinyl sulfoxide was added (62.25 g, 0.41 mol) and the resulting mixture was stirred for another 20 min. Additional portions of sodium hydride (0.5 g, 20 mmol) and phenyl vinyl sulfoxide (6.0 g, 39.4 mmol) were added and this mixture was stirred overnight. The reaction was quenched with acetic acid, extracted with water and concentrated in vacuo to give 1C which was used without further purification. i

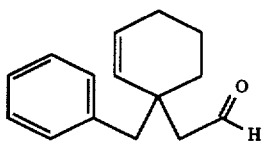
1D

Sodium bicarbonate (78.0 g, 0.93 mol) was added to a stirred solution of derivative 1C (77.39 g, 0.23 mol) in decalin (300 mL) under $N_2$. The reaction mixture was heated at reflux for 4 h, filtered through celite and the resulting filter cake was washed with $CH_2Cl_2$. The filtrate was concentrated in vacuo and the residue was purified by vacuum distillation to give aldehyde 1D as an oil (63 g).

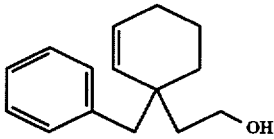
1E

A solution of aldehyde 1D (20 g, 0.0093 mol) in MeOH (300 mL) was added over 1.5 h, to a slurry of $NaBH_4$ (10.6 g, 0.28 mol) in MeOH (50 mL) at 0° C. After addition, the mixture was stirred at room temperature for 3 h and poured onto $H_2O$ (250 mL). The MeOH was removed in vacuo and $H_2O$ (100 mL) was added. This mixture was extracted with ethyl acetate and the organic extracts were dried, ($MgSO_4$) and concentrated in vacuo to give alcohol 1E as an oil (19.8 g).

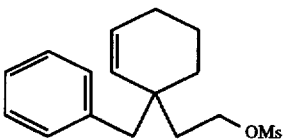
1F

Methanesulfonyl chloride (2.3 mL, 0.029 mol) was added to a solution of alcohol 1E (6.3 g, 0.029 mol) and triethylamine (8.7 mL, 0.062 mol) in $CH_2Cl_2$ (100 mL) at 0° C. under $N_2$. This mixture was stirred at 0° C. for 30 min and poured onto ice/$H_2O$ (200 mL). The resulting organic layer was dried ($MgSO_4$) and concentrated in vacuo to give the mesylate derivative 1F as an oil (6.5 g).

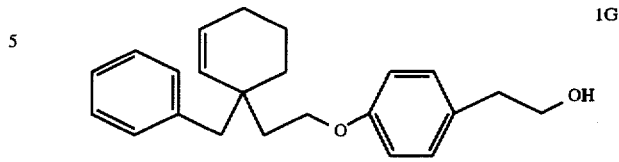
1G

A mixture of mesylate derivative 1F (5.0 g, 0.017 mol), 2-(4-hydroxyphenyl)-1-ethanol (3.1 g, 0.020 mol), $K_2CO_3$ (10 g, 0.072) in DMF (200 mL) was heated at 80° C. under $N_2$ for 48 h. The resulting mixture was cooled to 0° C. and diluted with $CH_2Cl_2$ and filtered. The filter cake was washed with several portions of $CH_2Cl_2$, concentrated in vacuo and purified by column chromatography (20% ethyl acetate/hexane) to give the alcohol derivative 1G as an oil (5.95 g).

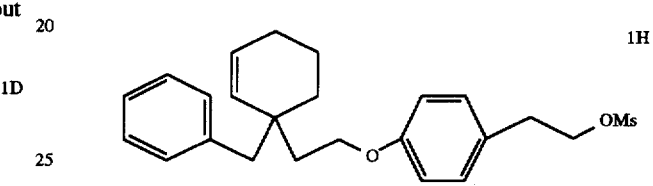
1H

Methanesulfonyl chloride (1.1 mL, 0.014 mol) was added dropwise to a solution of 1G (4.0 g, 0.012 mol), $Et_3N$ in $CH_2Cl_2$ (100 mL) at 0° C. under $N_2$. The reaction mixture was stirred for 30 min, an additional portion of methanesulfonyl chloride (0.5 mL, 0.007 mol) was added and the resulting mixture was stirred for another 2 h. Water was added and the resulting mixture was extracted with several portions of $CH_2Cl_2$. The combined organic extracts were dried ($Na_2SO_4$) and concentrated in vacuo to give the mesylate derivative 1H, as an oil (5.68 g).

Compound 1

1-(2-Aminoethyl)pyrrolidine (262.64 mg, 2.3 mmol) was added to a stirred solution of mesylate derivative 1H (888 mg, 2.143 mmol) in EtOH (50 mL) at room temperature under $N_2$. This mixture was heated at reflux for 16 h and concentrated in vacuo. The residue was purified by column chromatography (MeOH:$Et_3$N:hexanes, 5:5:90) to give an oil (65 mg). Said oil was treated with oxalic acid to give the title compound as an oxalate salt: mp 144–46° C.; IR (KBr, $cm^{-1}$) 2933, 2870, 1612, 1584; Anal. Calc'd for $C_{29}H_{40}N_2O \cdot C_2H_2O_4 \cdot 5H_2O$: Calculated: C, 70.05; H, 8.15; N, 5.27 Found: C, 70.17; H, 8.21; N, 5.61

The compounds listed in Table A were prepared using the method of Example 1. The appropriately substituted cyclohexene analogs of 1A were prepared from commercial starting materials in the same manner as 1A. These analogs were converted to their corresponding analogs of 1G as in Example 1. Finally the corresponding analogs of 1G were treated with known amines to give the compounds listed below.

TABLE A

Structure: cyclohexenyl-CR_a-CH_2CH_2-O-phenyl(R_b)_n

| Cpd.# | R_a | R_b | mp °C. | empirical formula | C | H | N |
|---|---|---|---|---|---|---|---|
| 17 | benzyl | 4-[(CH$_2$)$_2$NH$_2$] | 158–160 | C23 H29 N O. C2H2O4.1/4H2O | 69.89 | 7.36 | 3.59 |
| 22 | iso-propyl | 4-[(CH$_2$)$_2$NH$_2$] | 135–137 | C19 H29 N O. C2H2O4.1/4H2O | 66.08 | 8.43 | 3.88 |
| 23 | iso-propyl | 4-[(CH$_2$)$_2$NH(CH$_2$)$_2$-1-pyrrolidine] | 166–168 | C25 H40 N2 O. C2H2O4.1/2H2O | 66.64 | 8.70 | 5.76 |
| 62 | 4-CH$_3$-phenyl | 4-[(CH$_2$)$_2$NH$_2$] | 189–190 | C23 H29 N O. 1/2(C2H2O4).1/4H2O | 74.62 | 8.01 | 3.55 |
| 63 | 4-CH$_3$-phenyl | 4-[(CH$_2$)$_2$NH(CH$_2$)$_2$-1-pyrrolidine] | 145–147 | C29 H40 N2 O. C2H2O4.H2O | 68.78 | 7.86 | 5.12 |
| 64 | 4-CH$_3$-phenyl | 4-[(CH$_2$)$_2$NH(CH$_2$)$_3$N(CH$_3$)$_2$] | 170–172 | C28 H40 N2 O2. HCl.3/4H2O | 66.14 | 8.55 | 5.38 |
| 65 | 3-phenyl-prop-1-yl | 4-[(CH$_2$)$_2$NH$_2$] | 155–157 | C25 H33 N O.1/2(C2H2O4).H2O | 73.49 | 8.19 | 3.32 |
| 66 | 3-phenyl-prop-1-yl | 4-[(CH$_2$)$_2$NHCH$_2$)$_2$1-pyrrolidine] | 142–144 | C31 H44 N2 O. C2H2O4 | 71.84 | 8.73 | 5.23 |
| 33 | 4-Cl-benzyl | 4-[(CH$_2$)$_2$NH$_2$] | 145–147 | C23 H28 Cl N O. C2H2O4.1/2H2O | 63.64 | 6.71 | 3.04 |
| 68 | iso-propyl | 4-[(CH$_2$)$_2$NH(CH$_2$)$_3$N(CH$_3$)$_2$] | 173–175 | C24 H40 N2 O. 2HCl.3/4H2O | 62.79 | 9.68 | 6.25 |
| 34 | 4-Cl-benzyl | 4-[(CH$_2$)$_2$NH(CH$_2$)$_2$-1-pyrrolidine] | 175–177 | C29 H39 Cl N2 O. C2H2O4.3/2H2O | 63.66 | 7.23 | 4.71 |
| 36 | benzyl | 2-[(CH$_2$)$_2$NHCH$_3$] | 179–182 | C24 H31 N O. C2H2O4.1/4H2O | 70.47 | 7.53 | 3.17 |
| 37 | benzyl | 3-[(CH$_2$)$_2$NHCH$_3$] | 153–156 | C24 H31 N O. C2H2O4.1/4H2O | 70.58 | 7.53 | 3.16 |
| 69 | iso-propyl | 4-[(CH$_2$)$_2$NH$_2$] | 133–135 | C19 H29 N O. C2H2O4.1/2H2O | 65.43 | 8.21 | 3.60 |
| 39 | 3-Cl-benzyl | 4-[(CH$_2$)$_2$NH$_2$] | 135–137 | C23 H28 Cl N O. C2H2O4.1/2H2O | 63.66 | 6.55 | 2.96 |
| 40 | 3-Cl-benzyl | 4-[(CH$_2$)$_2$NH(CH$_2$)$_2$-1-pyrrolidine] | 145–147 | C29 H39 Cl N2 O. C2H2O4.1.5H2O | 63.64 | 7.35 | 5.06 |
| 41 | 4-OCH$_3$-benzyl | 4-[(CH$_2$)$_2$NH$_2$] | 110–112 | C24 H31 O2. C2H2O4.1/2H2O | 67.20 | 7.36 | 2.95 |
| 59 | 3,5-dichlorobenzyl | 4-[(CH$_2$)$_2$NH$_2$] | 158–161 | C23 H27 Cl2 N O. C2H2O4 | 60.42 | 5.71 | 2.74 |
| 60 | 3-Cl-benzyl | 4-[(CH$_2$)$_2$NHCH$_3$] | 124–127 | C25 H32 Cl N O. C2H2O4 | 66.28 | 6.94 | 2.77 |
| 61 | 3-Cl-benzyl | 4-[(CH$_2$)$_2$NH(CH$_2$)$_2$NH$_2$] | 168–171 | C25 H33 Cl N2 O. C2H2O4 H2O | 61.81 | 6.90 | 5.38 |

EXAMPLE 2

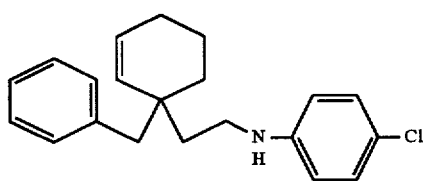

Compound 2

[N-[2-[1-BENZYL(2-CYCLOHEXENYL)]]ETHYL]-4-CHLOROANILINE MONOTOSYLATE.SESQUIHYDRATE 4-chloroaniline (267.1 mg, 2.1 mmol) and acetic acid (2 mL) was added to a solution of aldehyde 1D in MeOH (100 mL) under N$_2$ and the resulting mixture was stirred for 30 min. Sodium cyanoborohydride (131.96 mg, 2.1 mmol) was added and this mixture stirred for another 6 min. The resulting mixture was concentrated in vacuo, purified by column chromatography (4% ethyl acetate/hexane) and treated with toluene sulfonic acid in CH$_2$Cl$_2$ to give the title compound as a solid: mp 91–93° C.; IR (KBr, cm$^{-1}$) 3025, 2957, 2929, 2969, 1494; Anal. Calc'd for C$_{21}$H$_{24}$ClNO·C$_7$H$_8$O$_3$·0.2 5H$_2$O: Calculated: C, 66.92; H, 6.52; N, 2.79 Found: C, 66.98; H, 6.49; N, 2.85

The compounds listed in Table B were prepared using the method of Example 2. The appropriately substituted cyclohexene analogs of 1D were prepared from commercial starting materials in the same manner as 1D. These analogs were treated with known amines to give the compounds listed below.

TABLE B

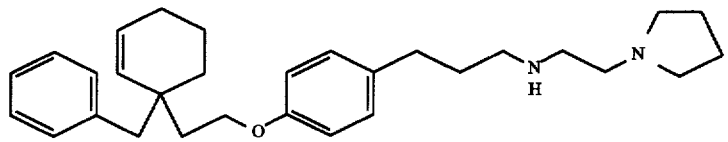

| Cpd# | R_a | R_b | mp °C. | empirical formula | C | H | N |
|---|---|---|---|---|---|---|---|
| 70 | benxyl | 4-CF$_3$ | 45–47 | C22 H24 F3 N. C7 H8 O3S.0.5H2O | 64.37 | 6.17 | 2.42 |
| 71 | benzyl | 3,5-Cl | 152–154 | C20 H23 Cl2 N. C7 H8 O3S.0.25H2O | 62.43 | 5.96 | 2.51 |
| 72 | benzyl | 2-Cl,5-OH | 168–170 | C21 H24 Cl N O. C7 H8 O3S.0.25H2O | 64.76 | 6.37 | 2.61 |
| 73 | benzyl | 3,4-Cl | 92–94 | C21 H23 Cl2 N. C7 H8 O3S | 62.98 | 5.86 | 2.69 |
| 74 | benzyl | 4-[(CH$_2$)$_2$—NH—Ac] | | | | | |

EXAMPLE 3

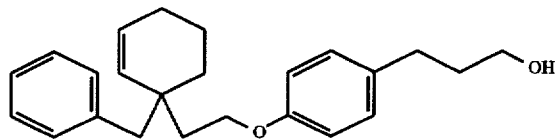

3-[3-[4-[2-[1-BENZLY-(2-CYCLOHEXENYL)]]ETHOXY]PHENYL-PROPYL] AMINOETHYL-PYRROLIDINE MONOOXALATE MONOHYDRATE
Compound 3

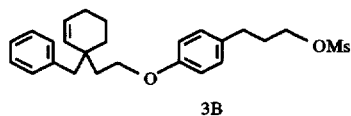

3A

A mixture of mesylate 1F (5.0 g, 17.00 mmol) (K$_2$CO$_3$) (39 g) and 3-(4-hydroxyphenyl)-1-propanol (3.1 g, 20 mmol) was heated at 80° C. under N$_2$ for 72 h. The mixture was cooled to 0° C., CH$_2$Cl$_2$ (100 mL) was added and the resulting precipitate was filtered. The combined filtrate was concentrated in vacuo and purified by column chromatography (20% ethyl acetate/hexane to give alcohol 3A as an oil (6.89 g).

3B

Methanesulfonyl chloride (1.5 mL, 19.4 mmol) was added dropwise to a stirred solution of triethylamine (4 mL, 28.7 mmol) and alcohol 3A (4.2 g, 12.0 mmol) in CH$_2$Cl$_2$ (100 mL) at 0° C. under N$_2$. The resulting mixture was poured into ice/H$_2$O (170 mL) and the aqueous layer was extracted with several portions of CH$_2$Cl$_2$. The combined organic layer was dried (Na$_2$SO$_4$) and concentrated in vacuo to give mesylate 3B as an oil (4.7 g).

Compound 3

A mixture of mesylate 3B (650 mg, 1.5 mmol), 1-(2-aminoethyl)pyrrolidine (700 mg, 6.1 mmol), K$_2$CO$_3$ (3 g, 21.7 mmol) in xylene (50 mL) was heated to 120° C. for 16 h and concentrated in vacuo. The residue was purified by column chromatography (ethyl acetate:methanol:Et$_3$N, 95:5:2) and treated with oxalic acid in ether to give the title compound as a solid: mp 152 (soften) ; IR (KBr, cm$^{-1}$) 2933, 2867, 2834, 1641, 1612; Anal. Calc'd for C$_{30}$H$_{42}$N$_2$O·C$_2$H$_2$O$_4$·H$_2$O: Calculated: C, 69.29; H, 8.36; N, 5.05 Found: C, 69.33; H, 8.12; N, 5.27

The compounds listed in Table C were prepared using the method of Example 3. The appropriately substituted cyclohexene analogs of 3B were prepared from commercial starting materials in the same manner as 3B. These analogs were treated with know amines to give the compounds listed below.

TABLE C

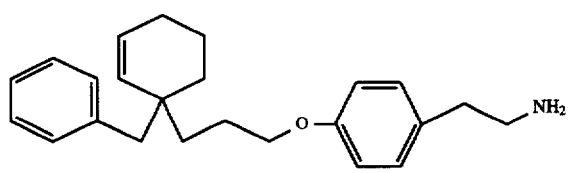

| Cpd# | R$_a$ | R$_b$ | mp °C. | empirical formula | C | H | N |
|---|---|---|---|---|---|---|---|
| 18 | benzyl | 4-[(CH$_2$)$_3$NH$_2$] | 104–107 | C24H31NO.C2H2)4. 0.25H2O | 69.57 | 7.77 | 3.12 |
| 19 | benzyl | 4-[(CH$_2$)$_3$NHCH$_3$] | 165–168 | C25 H33 NO. C2H2O4.0.5H$_2$O | 70.16 | 7.89 | 3.13 |
| 20 | benzyl | 4-[(CH$_2$)$_3$N(CH$_3$)$_2$] | 116–119 | C26 H35 NO. C2H2O4.0.5H$_2$O | 70.82 | 8.04 | 3.11 |
| 21 | benzyl | 4-[(CH$_2$)$_3$NH—(CH$_2$)$_2$-1-morpholine] | 173–176 | C30 H42 N2O2. C2H2O4.0.5H$_2$O | 68.36 | 8.22 | 4.99 |
| 24 | 4-fluorophenyl | 4-[(CH$_2$)$_3$NHCH$_3$] | 130–134 | C24 H30 FNO. C2 H2O4 | 68.08 | 7.37 | 2.82 |
| 25 | 4-fluorophenyl | 4-[(CH$_2$)$_3$NH(CH$_2$)$_2$OH] | 137–139 | C24 H30 FNO2. C2H2O4.0.25H$_2$O | 65.97 | 7.02 | 2.88 |
| 26 | 4-fluorophenyl | 4-[(CH$_2$)$_3$NH(CH$_2$)$_3$CH$_3$] | 175–178 | C27 H36 FNO. C2H2O4.0.25H$_2$O | 68.92 | 7.79 | 2.65 |
| 27 | 4-fluorophenyl | 4-[(CH$_2$)$_3$NH(CH$_2$)$_2$CH$_3$] | 168–169 | C26 H34 FNO. C2H2O4.0.25H$_2$O | 68.73 | 7.62 | 2.73 |
| 28 | 4-fluorophenyl | 4-[(CH$_2$)$_3$NHCH$_2$phenyl] | 198–201 | C30 H34 FNO. C2H2O4.0.25H$_2$O | 71.47 | 7.02 | 2.54 |
| 29 | 4-fluorophenyl | 4-[(CH$_2$)$_3$NH-cyclohexyl] | 163–165 | C28 H36 FNO. C2H2O4 | 70.39 | 7.80 | 3.12 |
| 31 | 3-phenyl-prop-1-yl | 4-[(CH$_2$)$_3$NHCH$_3$] | 137–140 | C27 H37 NO. C2H2O4 | 71.95 | 8.41 | 2.83 |
| 32 | butyl | 4-[(CH$_2$)$_3$NHCH$_3$] | 145–149 | C22 H35 NO. C2H2O4 | 68.79 | 8.90 | 3.24 |
| 35 | iso-propyl | 4-[(CH$_2$)$_3$NHCH$_3$] | 148–150 | C21 H33 NO. C2H2O4.0.25H$_2$O | 67.51 | 8.49 | 3.42 |
| 42 | 4-methoxybenzyl | 4-[(CH$_2$)$_3$NHCH$_3$] | 133–135 | C26 H35 N2O. C2H2O4.0.5H$_2$O | 68.40 | 7.95 | 2.80 |
| 43 | 4-methoxybenzyl | 4-[(CH$_2$)$_3$NH$_2$] | 110–112 | C25 H33 NO2. C2H2O4.0.75H$_2$O | 67.33 | 7.62 | 2.91 |
| 44 | 4-methoxybenzyl | 4-[(CH$_2$)$_3$NH(CH$_2$)$_2$-1-pyrrolidine] | 130–132 | C31 H44 N2O2. C2H2O4.1.5H$_2$0 | 66.88 | 8.11 | 4.72 |
| 52 | 4-chlorobenzyl | 4-[(CH$_2$)$_3$NH$_2$] | 130–132 | C24 H30 Cl NO. C2H2O4.0.75H$_2$O | 64.04 | 6.84 | 2.81 |

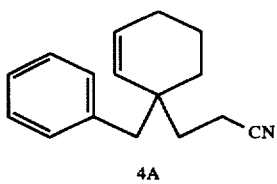

4-[3-[1-BENZYL-(2-CYCLOHEXENYL)]PROPOXY]PHEYETHYLAMINE MONOOXALATE HEMIHYDRATE
Compound 4

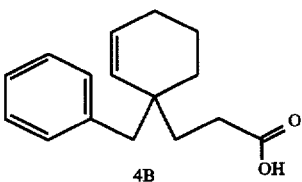

4A

KCN (1.8 g, 27.16 mmol) was added to a solution of mesylate derivative 1F (4.0 g, 13.58 mmol) in DMSO (50 mL) at room temperature under N$_2$. The resulting mixture was heated at 80° C. fro 16 h and partitioned between ether and H$_2$O. The organic layer was washed with several portions of H$_2$O and concentrated in vacuo. The residue was purified by column chromatography using ethyl acetate:hexanes (5:95–10:90) as an eluent to give the nitrile 4A as an oil (2.3 g).

4B

6N NaOH (25 mL)was added to a solution of nitrile 4A (2.3 g, 8.5 mmol) in MeOH (130 mL) at room temperature under N$_2$. This mixture was heated at at reflux for 16 h and concentrated in vacuo. The residue was treated with 6N HCl (150 mL) and H$_2$O (50 mL) and extracted with several portions of CH$_2$Cl$_2$. The organic layer was dried (MgSO$_4$) and concentrated in vacuo. The residue was purified by column chromatography using ethyl acetate:hexanes (5:95) to give the acid 4B as a solid (2.13 g).

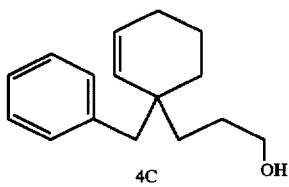

LAH (1.0 g, 26.35 mmol) was added to a solution of acid 4B (2.13 g, 7.40 mmol) in THF (100 mL) at room temperature under $N_2$ and the resulting mixture was stirred for 2 h. The reaction was cooled with ice and sat. $K_2CO_3$ (20 mL) was added. The resulting precipitate was removed and washed with several portions of $CH_2Cl_2$. This filtrate was concentrated in vacuo to give the alcohol 4C as an oil (2.12 g).

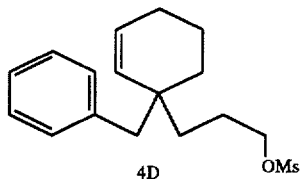

Methanesulfonyl chloride (7 mL, 9.2 mmol) was added dropwise to a stirred solution of alcohol 4D (2.12 g, 9.2 mmol), triethylamine (3 mL) and $CH_2Cl_2$ (200 mL) at 0° C. under $N_2$. The reaction mixture was stirred for 2 h and partitioned between $H_2O$ and $CH_2Cl_2$. The resulting organic layer was dried ($MgSO_4$) and concentrated in vacuo to give the mesylate 4D as an oil (4.39 g).

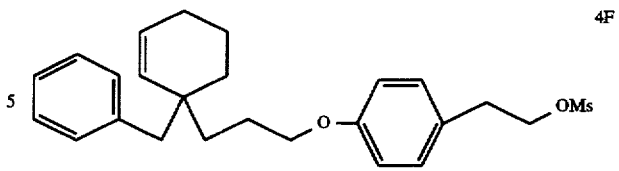

Methanesulfonyl chloride (0.5 g, 3.78 mmol) was added dropwise to a solution of 4E (1.2 g, 3.43 mmol) in $CH_2Cl_2$ (50 mL) at 0° C. under $N_2$. The reaction mixture was stirred for 2h. Water was added and the resulting mixture was extracted with several portions of $CH_2Cl_2$. The combined organic extracts were dried ($Na_2SO_4$) and concentrated in vacuo to give the mesylate derivative 4F, as an oil (1.28 g).

Compound 4

A mixture of ammonium hydroxide (3 mL), mesylate 4F (1.28 g, 2.94 mmol) in THF (20 mL) was placed in a sealed tube and heated at 100° C. for 16 h. The resulting mixture was partitioned between $H_2O$ and $CH_2Cl_2$ and the organic layer was concentrated in vacuo. The residue was purified by column chromatography using triethylamine:MeOH:ethyl acetate (5:5:90) as an eluent and treated with oxalic acid and ether to give the title compound as a solid: mp 140–142° C.; IR (KBr, $cm^{-1}$) 3083, 3027, 2989, 2836, 1700, 1652; Anal. Calc'd for $C_{24}H_{31}NO \cdot C_2H_2O_4 \cdot 0.5\ H_2O$: Calculated: C, 69.62; H,7.64; N,3.12 Found: C,69.52; H,7.51; N,3.12

The compounds in Table D were prepared using the method of Example 4.

Mesylate 4F was treated with a commercially available amine to give the desired compound.

TABLE D

| Cpd# | $R_a$ | $R_b$ | mp °C. | empirical formula | C | H | N |
|---|---|---|---|---|---|---|---|
| 30 | benzyl | 4-[$(CH_2)_2NHCH_3$] | 144–147 (dec) | C25 H33 NO. C2H2O4 | 71.30 | 7.80 | 2.83 |

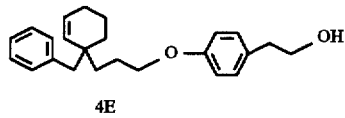

4E

A mixture of mesylate 4D (2.10 g, 6.7 mmol), 3-(4-hydroxyphenyl)-1-ethanol (1.4 g, 10.05 mmol), $K_2CO_3$ (4.0 g, 29.0 mmol) in DMF (100 mL) was heated at 100° C. for 24 h and concentrated in vacuo. The residue was purified by column chromatography using ethyl acetate:hexanes (5:95–30:70) as an eluent to give the alcohol 4E as an oil (1.2 g).

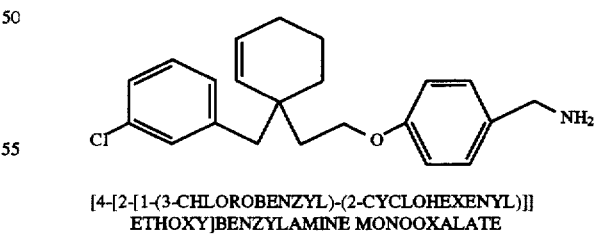

[4-[2-[1-(3-CHLOROBENZYL)-(2-CYCLOHEXENYL)]]ETHOXY]BENZYLAMINE MONOOXALATE

Compound 5

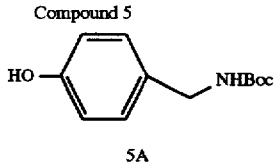

5A

Di-t-butyldicarbonate (19.0 g, 87 mmol) was added dropwise to a stirred suspension of 4-hydroxybenzylamine (12.0 g, 85 mmol; U.S. Pat. No. 4,388,250) in THF at 0° C. The reaction mixture was allowed to warm to room temperature, stirred for 16 h and concentrated in vacuo. The residue was stirred with $H_2O$ (250 mL) for 16 h and the resulting precipitate was isolated an dried in vacuo to give the alcohol 5A as a solid (21 g).

Compound 5

A mixture of the 3-chlorobenzyl derivative of mesylate 1F (2.35 g, 7.92 mmol), alcohol 5A (1.95 g, 8.7 mmol) and $K_2CO_3$ (2.5 g) in DMF was heated at 80° C. for 16 h. The reaction mixture was filtered, concentrated in vacuo and purified by column chromatography using ethyl acetate:hexanes (4:96–10:90) to give an oil. This oil was dissloved in 6 N HCl, heated to reflux for 16 h and concentrated in vacuo. The residue was purified by column chromatography using $Et_3N$:MEOH:ethyl acetate (5:2:93) and treated with oxalic acid to give the title compound as a solid: mp 150–153° C.; IR (KBr, $cm^{-1}$): 3100, 3050, 2930,1621, 1615; Anal. Calc'd for $C_{22}H_{26}ClNO \cdot C_2H_2O_4$; Calculated: C, 64.64; H, 6.33; N, 3.14 Found: C, 64.55; H, 6.32; N, 3.10

The compounds listed in Table E were prepared using the method of Example 5. The appropriately substituted alcohol derivatives 5A were prepared in the same manner as 5A and reacted with the appropriately substituted mesylate derivatives 1F as in Example 5.

-continued
Compound 6

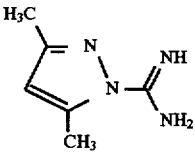

6A

Aminoguanidine nitrate (14.0, 0.1 mol) was added portionwise to a stirred mixture of 2,4-pentanedione (10 mL, 0.1 mol) in $H_2O$ (25 mL) and EtOH (25 mL) at reflux. The resultant mixture was stirred at reflux for 2.5 h, cooled to temperature and filtered to give the amidino pyrazole derivative 6A as a solid (9.4 g).

Compound 6

Derivative 6A (200.5 mg, ??), compound 5, and triethylamine (1 mL) in DMF (15 mL) was heated at 60° C. for 16 h and concentrated in vacuo. The residue was washed with several portions of ether and stirred in $H_2O$ for 8 h. The resulting solid was isolated and dried in vacuo to give the title compound as a solid: mp 128–130° C.; IR (KBr, $cm^{-1}$): 3380, 3190, 2938, 1669,1626; Anal. Calc'd for $C_{23}H_{28}ClN_3O \cdot HON_3$ Calculated: C, 59.93; H, 6.34; N, 12.15 Found: C, 59.81; H, 6.22; N, 11.79

TABLE E

| Cpd# | $R_a$ | $R_b$ | mp °C. | empirical formula | C | H | N |
|---|---|---|---|---|---|---|---|
| 46 | 4-methoxybenzyl | 4-$CH_2NH_2$ | 144–146 | C23 H29 N3 O2. HN03 | 65.57 | 7.22 | 3.15 |
| 54 | 4-methoxybenzyl | 2-$CH_2NH_2$ | 128–130 | C23 H29 N O2 C2H2O4.0.25H2O | 67.49 | 7.03 | 3.17 |
| 55 | 2-chlorobenzyl | 2-$CH_2NH_2$ | 132–135 | C22 H26 CL N O. C2 H2 O4 | 64.68 | 6.16 | 3.20 |
| 58 | 3,5-dichlorobenzyl | 3-$CH_2NH_2$ | 155–159 | C22H25 CL2 N O C2 H2 O4.0.25H2O | 59.37 | 5.72 | 2.92 |

EXAMPLE 6

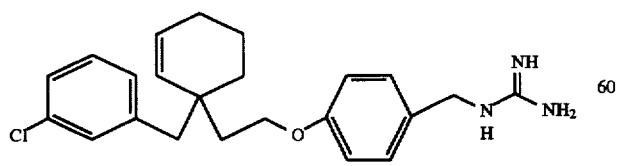

4-[2-[1-(3-CHLOROBENZYL)-(2-CYCLOHEXENYL)]ETHOXY] BENZYLGUANDINE MONONITRATE

The compounds listed in Table F were prepared using the method of Example 6 using the appropriately substituted amines prepared as cribed supra.

TABLE F

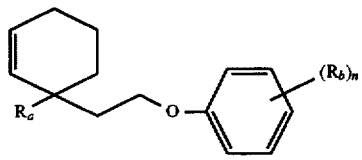

| Cpd# | R$_a$ | R$_b$ | mp °C. | empirical formula | C | H | N |
|---|---|---|---|---|---|---|---|
| 38 | benzyl | 4-[(CH$_2$)$_3$ guanidino] | 76–78 | C25 H33 N3O. HNO3.0.75H$_2$O | 64.07 | 7.33 | 11.88 |
| 53 | 4-methoxybenzyl | 4-[(CH$_2$)$_3$ guanidino] | 75–78 | C26 H33 N3O2. HNO3.0.25H$_2$O | 63.95 | 7.59 | 11.74 |
| 56 | 4-methoxybenzyl | 3-[(CH$_2$) guanidino] | 99–103 | C24 H31 N3O2. HNO3.0.25H$_2$O | 62.65 | 6.86 | 12.31 |
| 57 | 4-methoxybenzyl | 4-[(CH$_2$) guanidino] | 162–166 | C24 H31 N3O2. HNO3.0.25H$_2$O | 62.71 | 6.96 | 12.15 |
| 45 | 3-chlorobenzyl | 4-[(CH$_2$) guanidino] | 110–112 | C24 H30 Cl N3O. HNO3.0.5H$_2$O | 59.35 | 6.35 | 11.29 |
| 47 | 4-methoxybenzyl | 4-[(CH$_2$)$_2$ guanidino] | 125–127 | C24 H33 N3O2. HNO3 | 63.49 | 7.23 | 11.70 |

EXAMPLE 7

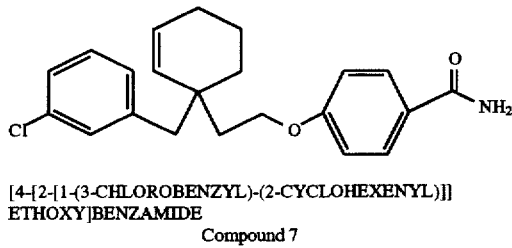

[4-[2-[1-(3-CHLOROBENZYL)-(2-CYCLOHEXENYL)]] ETHOXY]BENZAMIDE
Compound 7

A mixture of the 3-chlorobenzyl derivative of mesylate 1F (0.87 g, 2.7 mmol), 4-hydroxybenzamide (0.37 g, 3.7 mmol) and K$_2$CO$_3$ (0.7 g) in DMF (10 ml) was heated at 80° C. for 5 h, maintained at room temperature of 16 h and concentrated in vacuo. The residue was diluted with H$_2$O and extracted with several portions of ethyl acetate.. The combined organic layers were dried (MgSo$_4$) and concentrated vacuo. The residue was purified by column chromatography using ethyl acetate:hexanes (40:60) to give the title compound as a solid: mp 82°–84° C.; Anal. Calc'd for C$_{22}$H$_{24}$ClNO$_2$; Calculated: C, 71.44; H, 6.54; N, 3.79 Found: C, 71.05; H, 6.67; N, 3.47

The compounds listed in Table G were prepared using the method of Example 7.

TABLE G

| Cpd# | R$_a$ | R$_b$ | mp °C. | empirical formula | C | H | N |
|---|---|---|---|---|---|---|---|
| 51 | 4-methoxybenzyl | 4-amido | 85–88 | C23 H27 N O3 | 75.69 | 7.36 | 3.59 |

EXAMPLE 8

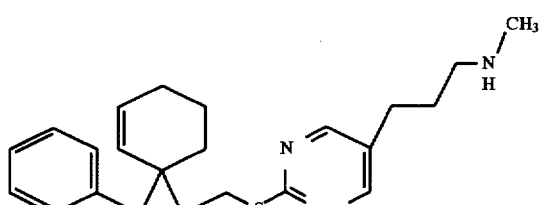

2-[[2-(1-BENZYLCYCLOHEX-2-ENYL)ETHYL]MERCAPTO]-
5-[3-(METHYLAMINO)PROPYL]PYRIMIDINE MONOOXALATE
Compound 8

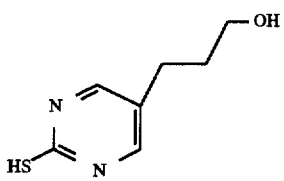

Thiourea (3.4 g, 45 mmol) was added to a prepared solution of sodiumisopropoxide (Na:IsOH, 2.0 g:150 mL) at room temperature and the resulting mixture was stirred for 15 min. 5,6-Dihydro-4H-pyran-3-carboxaldehyde (5 g, 45 mmol) was added and this mixture was stirred at reflux overnight, cooled to room temperature and concentrated in vacuo. The residue was purified by column chromatography using MeOH: $CH_2Cl_2$ (10:90) as an eluent and recrystallization from EtOH to give alcohol 8A as a solid (4.25 g).

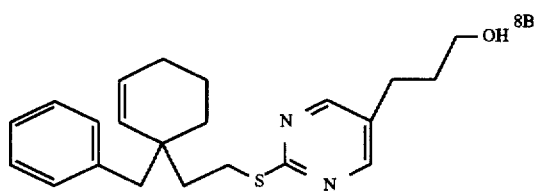

A mixture of mesylate 1F (2.4 g, 8.2 mmol), 8A (1.4 g, 8.2 mmol) and $K_2CO_3$ (2.6 g) in DMF (15 mL) was heated to 68° C. for 1 h. An additional portion of DMF was added (20 mL) and the reaction mixture was heated at 65° C. for another 30. The resulting mixture was concentrated in vacuo, diluted with $H_2O$ and extracted with several portions of ethyl acetate. The combined organic extracts were dried ($MgSO_4$), concentrated in vacuo and purified by column chromatography using MeOH:$CH_2Cl_2$ (5:95) as an eluent to give the coupled alcohol 8B (2.26 g).

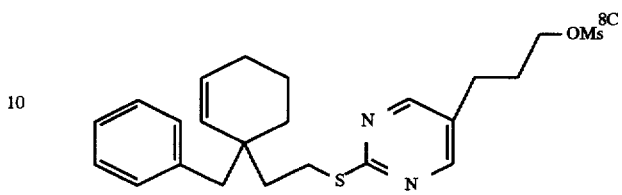

Methanesulfonyl chloride (0.15 mL, 1.94 mmol) was added to a stirred solution of triethylamine (0.5mL, 3.6 mmol), 11B (0.7 g, 1.97 mmol) in $CH_2Cl_2$ (30 mL) at 0° C. After 15 min the reaction mixture was poured into $H_2O$ and extracted with several portions of $CH_2Cl_2$. The combined extracts were dried ($MgSO_4$), concentrated in vacuo and purified by column chromatography using ether:hexanes (30:70) as an eluent to give the mesylate 8C.

Compound 8

A mixture of 8C (0.63 g, 1.4 mmol) and aqueous methylamine (5 mL) in THF (15 mL) was placed in a sealed tube and heated at 78°–80° C. for 5 h and concentrated in vacuo. The residue was diluted with ethyl acetate and washed with water. The organic extract was dried ($MgSO_4$), concentrated in vacuo and purified by column chromatography using MeOH:$CH_2Cl_2$ (10:90). The isolated material was treated with oxalic acid in acetone to give the title compound as a solid: mp 143°–145° C.; IR (KBr, cm$^{-1}$): 3064, 1705; Anal. Calc'd for $C_{23}H_{31}$ $N_3S \cdot C_2H_2O_4$ Calculated: C, 63.67; H, 7.05; N, 8.91 Found: C, 63.60;. H, 6.93; N, 8.73

The compounds listed in Table H were prepared using the method of Example 8. The required starting materials,3-(2-hydroxypyrimidinyl)-1-propanol, and 3-(4-pyrazolyl)-1-propanol were prepared by treating 5,6-dihydro-4H-pyran-3-carboxaldehyde with either guanidine hydrochloride or hydrazine in the manner used to prepare 8A. Those derivatives were treated in the same manner as 8A to give the desired compounds.

TABLE H

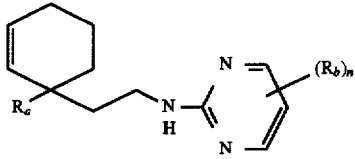

| Cpd# | $R_a$ | $R_b$ | mp °C. | empirical formula | C | H | N |
|---|---|---|---|---|---|---|---|
| 48 | benzyl | 4-[(CH$_2$)$_3$NHCH$_3$] | 125–129 | C23 H32 N4. C2 H2 O4 | 62.71 | 6.96 | 12.15 |
| 49 | benzyl | 4-[(CH$_2$)$_3$NH$_2$] | 143–145 | C22 H30 N4. C2 H2 O4 | 63.03 | 7.15 | 12.09 |

TABLE I

| Cpd# | R$_a$ | R$_b$ | mp °C. empirical formula | C | H | N |
|---|---|---|---|---|---|---|
| 50 | benzyl | 4-[(CH$_2$)$_3$ NHCH$_3$] | C22 H29 N3 S. C2 H2 O4.0.25 H2O | 62.23 | 6.77 | 3.59 |

EXAMPLE 9

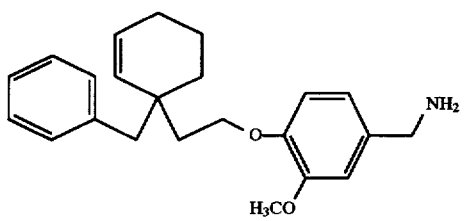

4-[2-[1-BENZYL(2-CYCLOHEXENYL)]]ETHOXY-3-METHOXYBENZYLAMINE MONOOXALATE HEMIHYDRATE
Compound 9

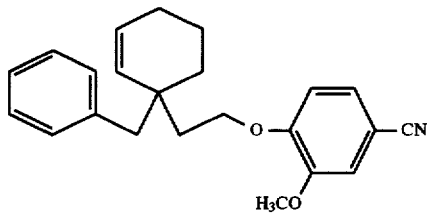

9A

4-Hydroxy-3-methoxybenzonitrile (2.56 g, 17.2 mmol) followed by K$_2$CO$_3$ (10 g) were slowly added to a solution of mesylate 1F (5.03 g, 17.09 mmol) in EtOH at 100° C. under N$_2$. This mixture was heated at reflux for 36 h, filtered and partitioned between H$_2$O and CH$_2$Cl$_2$. The combined organic extracts were dried (MgSO$_4$) and purified by column chromatography using ethyl acetate:hexanes (5:95–40:60) to give the nitrile 9A as an oil.

Compound 9

LAH (1.1 g, 38 mmol) was added to a stirred solution of nitrile 12A (971 mg, 2.8 mmol) in THF (200 mL) at 0° C. under N$_2$. The ice bath was removed and the reaction mixture was allowed to warm up to room temperature over 2h and heated at 80° C. for 16 h. The reaction was quenched by the addition of K$_2$CO$_3$ and the resulting white precipitate was removed by filtration through celite and washed with CH$_2$Cl$_2$. The filtrate was concentrated in vacuo and treated with ether an oxalic acid to give the title compound as a solid: mp 135°–137° C.; IR (KBr, cm$^{-1}$): 3082, 3063, 3004, 2935, 1608, 1593, 1518; Anal. Calc'd for C$_{23}$H$_{29}$N$_2$O·C$_2$H$_2$O$_4$·0.5H$_2$O; Calculated: C, 66.65; H, 7.16; N, 3.11 Found: C, 66.62; H, 7.03; N, 3.14

EXAMPLE 10

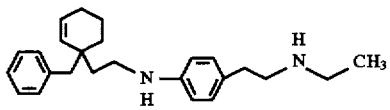

2-[4-[2-[1-BENZYL-2-(2-CYCLOHEXENYL)]]-ETHYLAMINOPHENYL]-N-ETHYLETHYL-AMINE MONOOXALATE HEMIHYDRATE
Compound 10

A suspension of LAH (400 mg, 10 mmol) and ether (100 mL) was added to a stirred solution of compound 74 (1.01 g, 2.6 mmol) in THF (20 mL) at 0° C. under N$_2$. After addition the reaction mixture was allowed to warm to room temperature and was stirred overnight. The reaction was quenched by the addition of K$_2$CO$_3$ and the resulting white precipitate was removed by filtration through celite and washed with CH$_2$Cl$_2$. The filtrate was concentrated in vacuo, purified by column chromatography using ethyl acetate:Et$_3$N:MEOH (96:5:1) and treated with oxalic acid to give the title compound as a solid: mp 154°–157° C.; IR (KBr, cm$^{-1}$): 3058, 3026, 2979, 2861, 1702, 1617; Anal. Calc'd for C$_{25}$H$_{34}$N$_2$·C$_2$H$_2$O$_4$·0.5H$_2$O; Calculated: C, 70.25; H, 8.08; N, 6.07 Found: C, 70.68; H, 8.16; N, 5.73

EXAMPLE 11

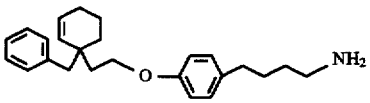

4-[4-[2-[1-BENZYL(2-CYCLOHEXENYL)]]-ETHOXY]PHENYLBUTYLAMINE MONOOXALATE HEMIHYDRATE
Compound 11

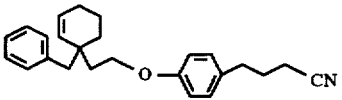

11A

A mixture of mesylate 3B (619 mg, 1.42 mmol), KCN (450 mg, 6.8 mmol) and Na (15 mg) in DMSO (20 mL) was stirred at 80° C. under N$_2$ for 16 h. The resulting mixture was diluted with ether, washed with several portions of H$_2$O. The combined organic extracts were dried (Na$_2$SO$_4$), concentrated in vacuo and purified by column chromatography using ethyl acetate:hexanes (10:90) to give nitrile 11A as a solid (275 mg).

Compound 11

A suspension of LAH (200 mg, 5.3 mmol) in ether (50 mL) was added to a solution of 14A (275 mg, 0.75 mmol) in ether (50 mL) under $N_2$ and the resulting mixture was stirred for 30 min. The reaction was quenched with $K_2CO_3$ and $H_2O$ and the resulting precipitate was filtered through celite and washed with $CH_2Cl_2$. The combined filtrate was concentrated in vacuo and treated with oxalic acid in ether to give the title compound as a solid: mp 162°–165° C.; 3051, 3016, 2957, 2835, 1718, 1622; Anal. Calc'd for $C_{25}H_{33}NO \cdot C_2H_2O_4 \cdot 0.5H_2O$; Calculated: C, 70.10; H, 7.84; N, 3.03 Found: C, 69.90; H, 7.94; N, 2.99

EXAMPLE 12

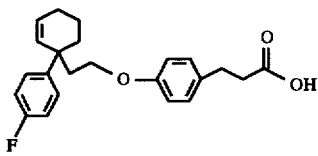

3-[4-[2-[1-(4-FLUOROPHENYL)-2-
CYCLOHEXENYL]ETHOXY]-
PHENYL] PROPIONIC ACID
MONOCYCLOHEXYLAMINE
SEQUIHYDRATE
Compound 12

Freshly prepared Jones Reagent was added over 10 min to a solution of the 4-fluoro derivative of alcohol 3A (344 mg, 1.0 mmol) in acetone (20 mL) at 0° C. After addition was complete, the reaction mixture was allowed to warm up to room temperature and was stirred for 3 h. MeOH (5 mL) was added, the resulting mixture was concentrated in vacuo and $H_2O$ was added. The oily residue was washed with several portions of $CH_2Cl_2$, and the combined organic layer was dried ($Na_2SO_4$), concentrated in vacuo and treated with cyclohexylamine and ether to give the title compound as a solid: mp 138°–141° C.; IR (KBr, cm$^{-1}$): 2943, 2903, 2835, 1637; Anal. Calc'd for $C_{23}H_{25}FO_3 \cdot C_6H_{13}N \cdot 0.25H_2O$; Calculated: C, 73.78; H, 8.22; N, 2.97 Found: C, 73.80; H, 8.18; N, 2.97

EXAMPLE 13

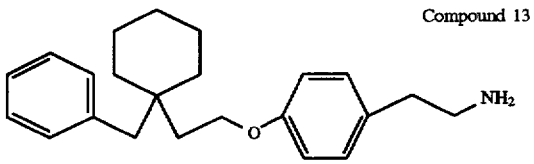

Compound 13

4-[2-(1-BENZYLCYCLOHEXYL)ETHOXY]PHENYLAMINE
MONOOXALATE 0.75 HYDRATE

A suspension of 4-[2-[1-benzyl-2-(cyclohexenyl)]]ethoxyphenethyl-2-t-butyl carbamate (100 mg, 0.23 mmol: prepared by the method of Example 1), $PtO_2$ (15 mg) in EtOH was agitated and treated with $H_2$ at 55 psi for 60 h. The mixture was filtered through celite, which was rinsed with $CH_2Cl_2$. The filtrate was concentrated in vacuo to give the amino protected saturated compound. This material was dissolved in TFA (10 mL),stirred at room temperature for 8 h and concentrated in vacuo. The residue partitioned between 1 N NaOH and $CH_2Cl_2$ and the resulting organic extracts were dried ($Na_2SO_4$) and concentrated in vacuo. The residue was dissolved in ether (25 mL) and treated with oxalic acid to give the title compound as a solid: mp 167°–169° C.; IR (KBr, cm$^{-1}$): 2943, 2903, 2835, 1637; Anal. Calc'd for $C_{23}H_{31}NO \cdot C_2H_2O_4 \cdot 0.75H_2O$; Calculated: C, 68.08; H, 7.88; N, 3.18 Found: C, 67.99; H, 7.66; N, 3.03

EXAMPLE 14

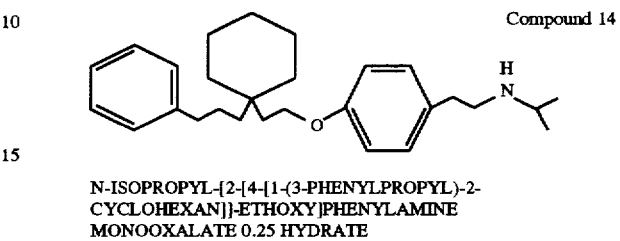

Compound 14

N-ISOPROPYL-[2-[4-[1-(3-PHENYLPROPYL)-2-
CYCLOHEXAN]]-ETHOXY]PHENYLAMINE
MONOOXALATE 0.25 HYDRATE

An agitated suspension of 2-[4-[2-[1-(3-phenylpropyl)-2-cyclohexenyl]]ethoxy]-phenylethylamine hemioxalate monohydrate (205 mg, 2.08 mmol) 6N HCl (3 mL), $PtO_2$ (10 mg) and acetone (5 mL) in EtOH (25 mL) was treated with $H_2$ at 45 psi for 8 h. The resulting mixture was filtered through celite and the filter cake was washed with $CH_2Cl_2$. The combined organic extracts were washed with 1 N NaOH, dried ($Na_2SO_4$) and concentrated in vacuo. The residue was dissolved in ether and treated with oxalic acid to give the title compound as a solid: mp 135°–137° C.; IR (KBr, cm$^{-1}$): 2851, 1703, 1613; Anal. Calc'd for $C_{28}H_{41}NO \cdot C_2H_2O_4 \cdot 0.25H_2O$; Calculated: C, 71.75; H, 8.73; N, 2.79 Found: C, 71.56; H, 9.09; N, 2.76

EXAMPLE 15

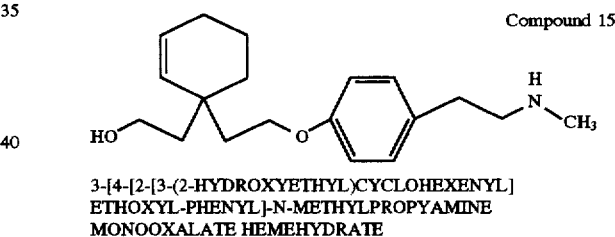

Compound 15

3-[4-[2-[3-(2-HYDROXYETHYL)CYCLOHEXENYL]
ETHOXYL-PHENYL]-N-METHYLPROPYAMINE
MONOOXALATE HEMEHYDRATE

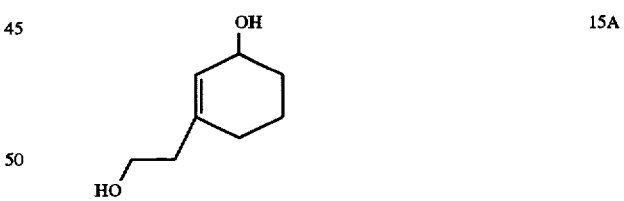

15A

3-Ethoxymethyl-2-cyclohexen-1-one ( 15.0 g, 82 mmol) was added dropwise to a stirred suspension of LAH (6.0 g, 164 mmol) in ehter (300 mL) at 0° C. under $N_2$. The mixture was stirred for 5 h, quenched by adding aqueous $K_2CO_3$, stirred for another 16 h and filtered through celite. The organic layer was dried ($Na_2SO_4$) and concentrated in vacuo to give the alcohol 15A as an oil (8.66 g).

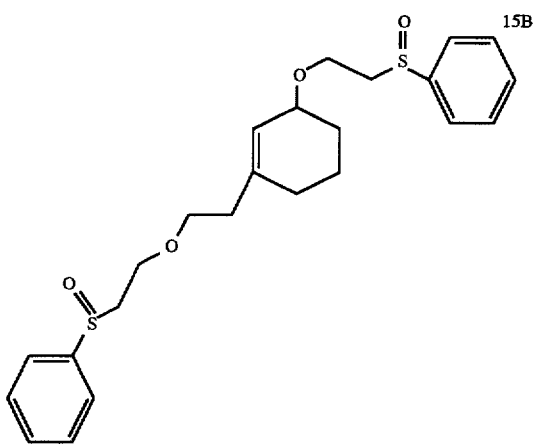

Sodium hydride (270 mg, 11.25 mmol) was added in portions to a stirred solution of 15A (1.0 g, 7.04 mmol) in THF (150 mL) at room temperature under $N_2$. After 30 min of stirring, phenyl vinyl sulfoxide (2.64 g, 17.6 mmol) was added and the resulting mixture was stirred for 16 h. The reaction was quenched with $H_2O$, extracted with successive portions of ether as well as ethyl acetate and the combined organic extracts were concentrated in vacuo to give 15B as an oil (5.6 g).

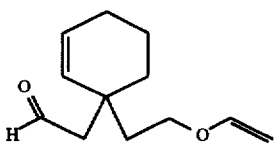

A stirred mixture of $NaHCO_3$ (5.0 g), 15B (5.6,12.55 mmol) in decalin (50 mL) was heated at 180° C. for 4 h and filtered through celite. The filter cake was washed with $CH_2Cl_2$ and the filtrate was concentrated in vacuo and purified by distillation to give the aldehyde derivative 15C as an oil (585 mg).

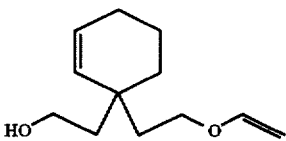

A solution of 15C (222.3 mg, 2.99 mmol) in EtOH (100 mL) was added over 1.5 h to a stirred slurry of $NaBH_4$ (110.6 mg, 2.99 mmol) at 0° C. The resulting mixture was stirred for 4 h poured onto ice/$H_2O$ (100 mL), concentrated in vacuo and partitioned between $H_2O$ and $CH_2Cl_2$. The resulting organic layer was dried ($Na_2SO_4$) and concentrated in vacuo to give the alcohol 15D as a crude oil (430 mg).

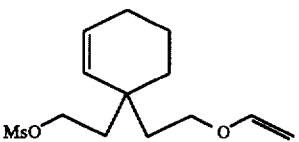

Methanesulfonyl chloride (222.3 mg, 1.95 mmol) was added dropwise to a stirred solution of 15D (380 mg, 1.94 mmol) and triethylamine (4 mL) in $CH_2Cl_2$ (150 mL) at 0° C. under $N_2$. This mixture was stirred for 1 h and partitioned between $H_2O$ and $CH_2Cl_2$. The organic layer was dried ($Na_2SO_4$) and concentrated in vacuo to give mesylate 15E as an oil (612 mg).

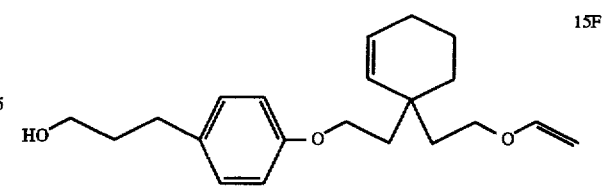

A mixture of 15E (612 mg, 2.23 mmol), $K_2CO_3$ (100 mg) and 3-(4-hydroxypheny)-1-propanol (407.7 mg, 2.68 mmol) in DMF (150 mL) was heated at 80° C. under $N_2$ for 16 h. The resulting mixture was cooled to 0° C., diluted with $CH_2Cl_2$, filtered and purified by column chromatography (EtOAc:hexanes, 20:80) to give the aromatic alcohol 15F as an oil (183 mg).

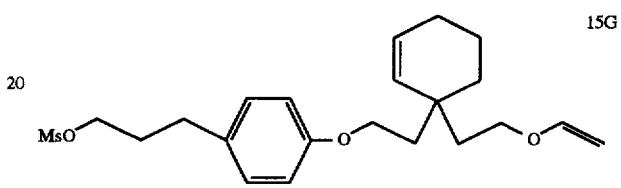

Methanesulfonyl chloride (70 mg, 0.56 mmol) was added dropwise to a stirred solution of 15F (183 mg, 0.55 mmol) and triethylamine (2 mL) in $CH_2Cl_2$ (100 mL) at 0° C. under $N_2$. This mixture was stirred for 15 h and partitioned between $H_2O$ and $CH_2Cl_2$. The resulting organic layer was separated, dried ($Na_2SO_4$) and concentrated in vacuo to give the mesylate 15G as an oil (180 mg).

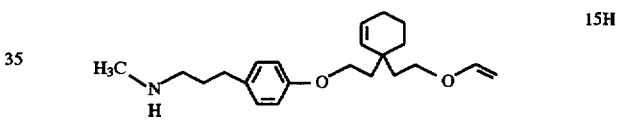

A mixture of 10% $CH_3NH_2$/THF (3 mL), 15G (180 mg, 0.44 mmol) in THF (10 mL) was placed in a sealed tube and heated at 70° C. for 16 h. The mixture was partitioned between $H_2O$ and $CH_2Cl_2$ and the organic layer was separated and concentrated in vacuo. The residue was purified by column chromatography (triethylamine:MeOH:ethyl acetate; 5:10:85) to give amine 15H as a pale yellow oil (110 mg).

Compound 15

Amine 15H (1 10 mg) was treated with oxalic acid and ether to give title compound as a solid: mp 115°–117° C.; IR (KBr, $cm^{-1}$): 3010, 3002, 2938; Anal. Calc'd for $C_{20}H_{3}NO_2 \cdot C_2H_2O_4 \cdot 0.5H_2O$; Calculated: C, 63.44; H, 8.23; N, 3.36 Found: C, 63.47;. H, 8.06; N, 3.36

EXAMPLE 16

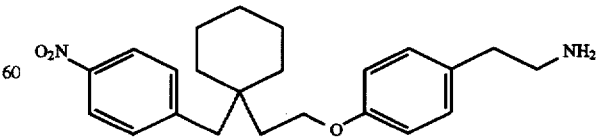

4-{2-[1-(4-NITROBENZYL)CYCLOHEXYL]ETHOXY} PHENETHYLAMINE MONOOXALATE HEMIHYDRATE
Compound 16

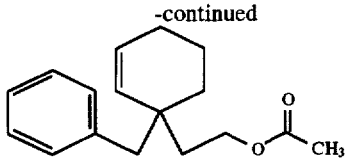
16A

A solution of alcohol 1E (1.0 g, 4.65 mmol) and acetic anhydride (4 mL) in CH$_2$Cl$_2$ (50 mL) was stirred at room temperature of 30 min. DMAP (10 mg) was added and this mixture was stirred for 1 h and diluted with CH$_2$Cl$_2$. The resulting mixture was washed with water and the combined organic extracts were dried (Na$_2$SO$_4$) and concentrated in vacuo to give acetate 16A as an oil (1.2 g).

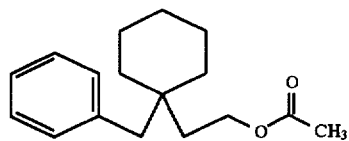
16B

A mixture of 16B (800 mg, 3.10 mmol) acetic acid (2 mL) and PtO$_2$ (20 mg) in EtOH (25 mL) was placed on a hydrogenation apparatus and treated with H$_2$ at 55 psi for 6 h. The resulting mixture was filtered through celite and the filter cake was washed with CH$_2$Cl$_2$. The combined organic extracts were concentrated in vacuo to give the saturated derivative 16B as an oil (510 mg).

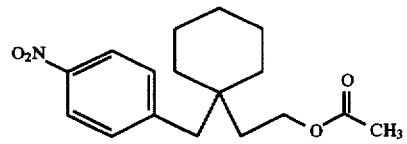
16C

A mixture of 16C (510 mg, 1.96 mmol) and HNO$_3$/H$_2$SO$_4$ (1.2/0.64 mL) at 0° C. under N$_2$ was stirred for 30 min. The mixture was partitioned between aq. NaOH and ether. The organic layer was dried (Na$_2$SO$_4$) and purified by column chromatography using ethyl acetate:hexane (10:90) as an eluent to give the nitro intermediate 16C as a solid (350 mg).

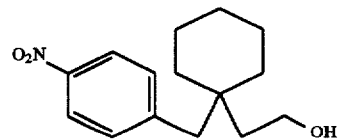
16D

A solution of aqueous K$_2$CO$_3$ (20 mg/10 mL) was added to a stirred solution of 16C (350 mg) in MeOH (50 mL). This mixture was stirred for 1 h, concentrated in vacuo and partitioned between H$_2$O and ethyl acetate. The resulting organic layer was dried (Na$_2$SO$_4$) and concentrated in vacuo to give alcohol 16D as an oil (300 mg).

Compound 16

Alcohol 16D was treated in the same manner, following the same reaction sequence as intermediate 1E of Example 1 to give Compound 16 as a solid:mp 120°–123° C.; IR (KBr, cm$^{-1}$): 2939, 1298, 1238; Anal. Calc'd for C$_{23}$H$_{30}$N$_2$O$_3$·C$_2$H$_2$O$_4$·0.5H$_2$O; Calculated: C, 62.36; H, 6.91; N, 5.82 Found: C, 62.12; H, 6.95; N, 6.21

We claim:

1. A method of treating bacterial infections in mammals which comprises administering to said mammal an antibacterially effective amount of a compound having activity as a histidine protein kinase inhibitor selected from those of the Formula I:

I wherein:

R$_1$ is selected from branched or unbranched (C$_1$–C$_6$)alkyl, (C$_1$–C$_6$) hydroxyalkyl, and a moiety of the formula:

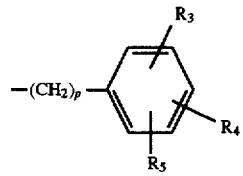

wherein:

p is an integer from 0–6;

and R$_3$, R$_4$ and R$_5$ are independently selected from hydrogen, halo, (C$_1$–C$_4$) alkyl, (C$_1$–C$_4$) alkoxy, hydroxy, hydroxyalkyl, amino, (C$_1$–C$_4$) alkylamino, and nitro;

n is an integer from 1–6;

q is an integer from 0–2;

X is selected from O and S;

R$_2$ is selected from phenyl and a heterocyclic moiety wherein the heterocyclic moiety is a monocyclic heterocyclic group having 5 or 6 ring atoms and 1–4 nitrogen, oxygen, or sulfur atoms and is saturated or unsaturated, and wherein the phenyl or heterocyclic moiety is substituted with amino, moieties of the formula:

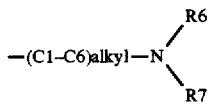

carboxy, carboxy(C$_1$–C$_6$)alkyl, (C$_1$–C$_6$)alkylcarboxy, or a moiety of the formula:

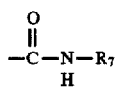

and, optionally, 1–3 substituents selected from oxo, halo, trifluoromethyl, hydroxy, -(C$_1$–C$_6$) alkyl and (C$_1$–C$_6$) alkoxy;

wherein R$_6$ is selected from hydrogen and (C$_1$–C$_6$)alkyl;

R$_7$ is selected from hydrogen, (C$_1$–C$_6$) alkyl, (C$_3$–C$_6$) cycloalkyl, (C$_1$–C$_6$) hydroxyalkyl, (C$_1$–C$_6$)acyl, a moiety of the formula:

and a moiety of the formula

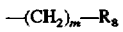

wherein m is an integer from 1–4; and

R$_8$ is selected from amino, amino(C$_1$–C$_6$)alkyl, amino((C$_1$–C$_6$)alkyl)$_2$, an aryl group and a heterocyclic group wherein the aryl group is a monocyclic or bicyclic aromatic hydrocarbon group having from 6 to 10 carbon atoms and the heterocyclic group is a monocyclic or bicyclic group of 4–10 ring atoms wherein the heteroatom or heteroatoms are selected from 1–4 oxygen, nitrogen or sulfur atoms and each ring of the heterocycle is composed of 4–6 atoms and is saturated or unsaturated; and the pharmaceutically acceptable salts thereof.

2. A method according to claim 1 wherein $R_1$ is selected from branched or unbranched $(C_1-C_6)$ alkyl, $(C_1-C_6)$ hydroxyalkyl, and a moiety of the formula:

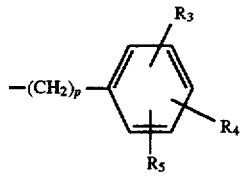

wherein p is an integer from 0–6;

and $R_3$, $R_4$ and $R_5$ are independently selected from hydrogen, halo, $(C_1-C_4)$ alkyl, and $(C_1-C_4)$ alkoxy;

n is an integer from 1–3;

X is O or S;

$R_2$ is selected from phenyl, pyrimidine, pyrimidone and pyrazole and $R_2$ is substituted with amino, moieties of the formula;

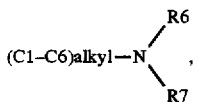

carboxy, $(C_1-C_6)$alkylcarboxy, carboxy$(C_1-C_6)$alkyl, and a moiety of the formula:

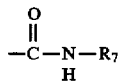

and, optionally 1–3 substituents selected from oxo, halo, trifluoromethyl, hydroxy, -$(C_1-C_6)$alkyl, and $(C_1-C_6)$ alkoxy;

wherein $R_6$ is selected from hydrogen and $(C_1-C_6)$alkyl; and $R_7$ is selected from hydrogen, $(C_1-C_6)$ alkyl, $(C_4-C_6)$ cycloalkyl, $(C_1-C_6)$ hydroxyalkyl, a moiety of the formula:

and a moiety of the formula:

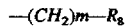

wherein m is an integer from 1–4; and

R8 is selected from amino, amino$(C_1-C_6)$alkyl and phenyl, benzyl, pyrrolidine, morpholine, and indole;

and the pharmaceutically acceptable salts thereof.

3. A compound of the Formula I:

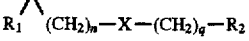

wherein:

R1 is benzyl optionally substituted with one to three substituents independently selected from halo, $(C_1-C_4)$ alkyl, and $(C_1-C_4)$alkoxy;

n is an integer from 1–3;

X is selected from O and S;

q is an integer from 0–2;

$R_2$ is selected from phenyl, pyrimidine, pyrimidone and pyrazole and $R_2$ is substituted with amino, moieties of the formula;

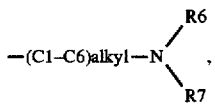

carboxy, $(C_1-C_6)$alkylcarboxy, carboxy$(C_1-C_6)$alkyl, or a moiety of the formula:

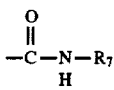

and, optionally 1–3 substituents selected from oxo, halo, trifluoromethyl, hydroxy, -$(C_1-C_6)$alkyl, and $(C_1-C_6)$ alkoxy;

wherein $R_6$ is selected from hydrogen and $(C_1-C_6)$alkyl; and $R_7$ is selected from hydrogen, $(C_1-C_6)$ alkyl, $(C_4-C_6)$ cycloalkyl, $(C_1-C_6)$ hydroxyalkyl, a moiety of the formula:

and a moiety of the formula:

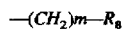

wherein m is an integer from 1–4; and

R8 is selected from amino, amino$(C_1-C_6)$alkyl and phenyl, benzyl, pyrrolidine, morpholine, and indole;

and the pharmaceutically acceptable salts thereof.

4. A compound according to claim 3 wherein:

X is oxygen, $R_2$ is a moiety selected from those of the formulae:

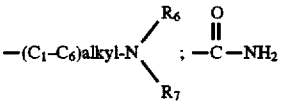

$R_6$ and $R_7$ are both hydrogen and $R_1$, and n are as defined in claim 3.

5. The compound according to claim 3, [4-[2-[1-(3-CHLOROBENZYL)-(2-CYCLOHEXENYL)]]ETHOXY] BENZYLAMINE MONOOXALATE.

6. The compound according to claim 3, 4-[2-[1-(3-CHLOROBENZYL)-(2-CYCLOHEXENYL)]ETHOXY]BENZYLGUANIDINE MONONITRATE.

7. The compound according to claim 3, 3-[3-[4-[-[1-BENZYL-(2-CYCLOHEXENYL)]]ETHOXY]PHENYLPROPYL]AMINOETHYL-PYRROLIDINE MONOOXALATE MONOHYDRATE.

8. The compound according to claim 3,4-[3-[1-BENZYL-(2-CYCLOHEXENYL)]PROPOXY]PHENETHYLAMINE MONOOXALATE HEMIHYDRATE.

9. The compound according to claim 3, 4-[2-[1-BENZYL(2-CYCLOHEXENYL)]]ETHOXY-3-METHOXYBENZYLAMINE MONOOXALATE HEMIHYDRATE.

10. The compound according to claim 3, 3-[4-[2-[1-(4-FLUOROPHENYL)-2-CYCLOHEXENYL]ETHOXY]-PHENYL]PROPIONIC ACID MONOCYCLOHEXYLAMINE SEQUIHYDRATE.

11. The compound 4-[4-[2-[1-BENZYL(2-CYCLOHEXENYL)]]ETHOXY]PHENYLBUTYLAMINE MONOOXALATE HEMIHYDRATE.

12. A pharmaceutical composition for treating bacterial infections comprising an effective amount of a compound selected from claim 1 in association with a pharmaceutically acceptable carrier.

13. A pharmaceutical composition for treating bacterial infections comprising an effective amount of a compound selected from claim 2, in association with a pharmaceutically acceptable carrier.

14. A pharmaceutical composition for treating bacterial infections comprising an effective amount of a compound selected from claim 3 in association with a pharmaceutically acceptable carrier.

15. A pharmaceutical composition for treating bacterial infections comprising an effective amount of a compound selected from claim 4 in association with a pharmaceutically acceptable carrier.

16. A method of treating bacterial infections in mammals which comprises administering to said mammal an antibacterially effective amount of a compound selected from those of claim 3.

17. A method of treating bacterial infections in mammals which comprises administering to said mammal an antibacterially effective amount of a compound selected from those of claim 4.

* * * * *